United States Patent [19]

Cecinati et al.

[11] Patent Number: 4,907,278

[45] Date of Patent: Mar. 6, 1990

[54] INTEGRATED PROCESSING UNIT, PARTICULARLY FOR CONNECTED SPEECH RECOGNITION SYSTEMS

[75] Inventors: Riccardo Cecinati, Albisola Superiore; Alberto Ciaramella, Rosta; Luigi Licciardi, Almese; Maurizio Paolini, Turin; Robert Tasso, Alessandria; Giovanni Venuti, San Maurizio Can.se, all of Italy

[73] Assignee: Presidenza Dei Consiglio Dei Ministri Del Ministro Per Il Coordinamento Delle Iniziative Per La Ricerca Scientifica E Tecnologica, Dello Stato Italiano, Rome, Italy

[21] Appl. No.: 211,812

[22] Filed: Jun. 27, 1988

[30] Foreign Application Priority Data

Jun. 25, 1987 [IT] Italy ............................. 21037 A/87

[51] Int. Cl.$^4$ ................................................ G01L 5/00
[52] U.S. Cl. .................................... 381/43; 364/513.5
[58] Field of Search ................................... 381/42–43; 364/513.5

[56] References Cited

U.S. PATENT DOCUMENTS 4,713,778 12/1987 Baker ..................................... 381/43
4,720,864 1/1988 Tajima et al. ......................... 381/43
4,776,016 10/1988 Hanson ............................. 364/513.5

Primary Examiner—Emanuel S. Kemeny
Attorney, Agent, or Firm—Herbert Dubno

[57] ABSTRACT

This connected-speech recognition system uses a two-level hierarchical system, in which the higher-level (master) processor and one or more lower-level units (slaves) process, respectively, the most probably word sequence within a permitted grammar network, and the likelihood of individual words with the grammar network. The lower-level processing performs dynamic programming involving vector and matrix calculation and comparison, and processing speed is improved by an integrated processing unit which has simultaneous access to the external data memory as well as to a high-speed internal microinstruction ROM. One of the aforementioned units can also provide for performing an additional internal test function. The structure features two internal data buses and internal memories for more commonly used data and addresses, for enabling high-speed microinstruction performance and external memory access. The external memory is divided into tables differing structurally but such as to be accessed in uniform manner by the internal addressing unit.

9 Claims, 18 Drawing Sheets

INTEGRATED PROCESSING UNIT, PARTICULARLY FOR CONNECTED SPEECH RECOGNITION SYSTEMS

FIELD OF THE INVENTION

Our present invention relates to microprogrammed integrated circuits and, more particularly, to an integrated processing unit particularly suitable for employment in connected speech recognition systems.

The microprogrammed integrated circuit according to the present invention is particularly, though not exclusively, suitable for performing the function of a lower-level processing unit in a multilevel hierarchical processing system.

In a two-level hierarchical system featuring a higher-level processing unit (master) and one or more lower-level units (slaves), the circuit according to the present invention performs the function of one of the slave units.

The two-level hierarchical system may be employed to advantage for performing a two-level hierarchical algorithm for connected speech recognition.

Of connected speech recognition algorithms, particularly effective are those enabling sentence recognition as the sentence is acquired, as opposed to recognition at the end of the sentence. One class of such algorithms is organized on two hierarchical levels, of which the higher level searches out the most probable word sequence within a grammar network of permitted word sequences, while the lower level checks the likelihood of individual words within the said grammar network.

BACKGROUND OF THE INVENTION

There is a known class of HDP (Hierarchical Dynamic Programming) algorithms, which provide for easy vocabulary expansion and a marked distinction between the types of operations performed at each hierarchical level. The lower level performs known dynamic programming operations involving vector and matrix calculation and comparison.

A major problem encountered in the design of lower-level processing units is microinstruction performance speed and external data memory access speed, for enabling predominantly real-time processing which is very burdensome.

SUMMARY OF THE INVENTION

This problem is solved by the present invention, which relates to an integrated processing unit, particularly suitable for connected speech recognition systems, which has simultaneous access to the external data memory as well as to a highly parallel, high-speed internal ROM microprogram memory.

The internal structure of the device features two data buses, the sources and destinations of which are so distributed as to practically eliminate waiting due to unavailability of the internal bus.

For minimizing access demand on the external memories, provision has been made for internal memories storing more commonly used data and addresses, and an optimized access procedure has been provided for matrix data structures.

The external data memories are employed in particular for local dynamic programming parameter storage, and the address memories for fast build up of addresses for access to the external data memory.

The device presents a distance-computing arithmetical unit (positive 12-bit-saturated arithmetics) and addressing circuits enabling access to the external memories every two internal microinstructions. The external memory is divided into tables, each consisting of a number of appropriately ordered records. Though each table presents a different record structure, table access address acquisition by the addressing unit, also using basic addresses stored in the internal memories, is standardized for speeding up the procedure.

For increasing microprogram performance speed, use is also made of conditional operations, i.e. performed differently according to the logic level of a condition bit, which arrangement provides for greater efficiency as compared with a yes or no conditional branch.

The device also provides for an additional internal test function carried out by dividing the procedure into independently performable subroutines stored in the microprogram memory in such a manner as to enable initiation of each subroutine by simply forcing the starting address from the outside. In each subroutine, the test result is calculated by an internal circuit, which generates a cyclic redundancy code of the test data on an internal bus, and is written into a subsequently outgoing status word.

The processing unit according to the present invention may be employed for word representation via either prototypical or Markov models (discussed in more detail later on) by simply modifying a bit in a control word supplied by the master.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
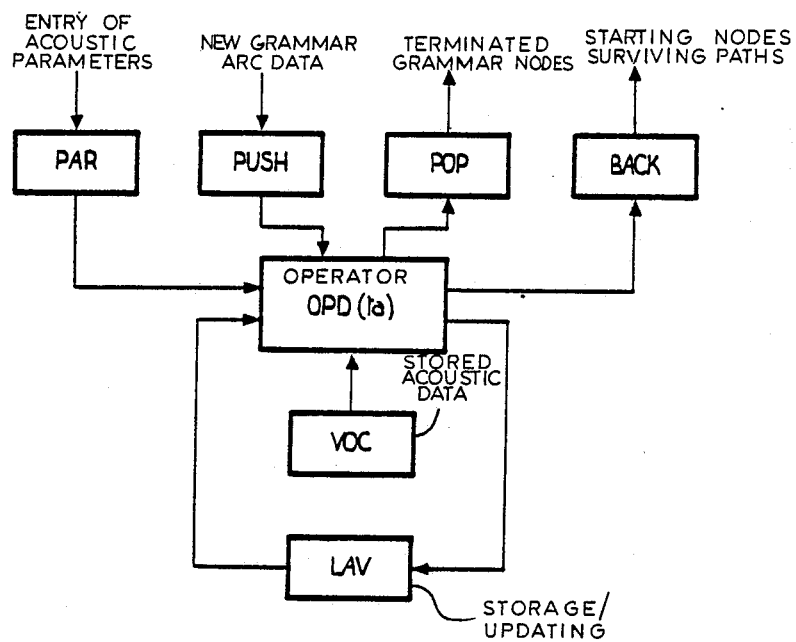
FIG. 1 shows a block diagram of the table structure and operation of the external memory.

The following is a brief description of the operation (substantially known) of two-level HDP algorithms for connected speech recognition.

A voice signal may be defined quite simply as a discrete sequence of parameter vectors, each representing a signal "spectral state". The vectors are obtained by acoustically analyzing a portion of the signal, and substantially represent the power spectrum of the signal or a transformation of the same. The signal portion is analyzed at regular intervals wherein the signal may reasonably be assumed to be stationary. The parameter vector may also undergo further coding, via vector quantization, which consists in comparing the input vector with a reference vector codebook and assigning it a symbol consisting of the index of the closest resembling vector index in the codebook.

Connected speech is intended to mean a more or less long group of word sequences (or sentences). The HDP class of algorithms only considers word sequences defined by a grammar network in the form of a group of arc-connected nodes. Each arc represents a word of the vocabulary, and a given word may appear on more than one arc, i.e. in different sentences or at different points of a given sentence defining the various word contexts. The locations of the nodes and node connecting arcs define the word sequences permitted by the network.

This representation is also known as a "finite state automation", the finite states being the grammar network nodes, which may also be considered the start and end points of the words.

A silence word also exists, consisting of a single spectral state representing the background noise spectrum. In addition to being inserted at the start and end of each sentence, this word is also inserted between the words in the sentence and may be repeated indefinitely.

Each word may in turn be represented by a finite state automation.

Words may be represented according to two basic methods: using "prototypical" or "Markov" models.

When using prototypical models, each automation state s is assigned a corresponding spectral state as defined above, and the automaton arcs define the permitted spectral state transitions.

When using Markov models, each automaton state s is assigned two matrixes: an emission matrix containing the probability vectors that, in state s, the model may emit each of the spectral state symbols, and a transition matrix containing the probabilities of passing from state s to another automaton state. The probability vectors in both matrixes are calculated via a known iterative training procedure.

In the case of connected speech recognition featuring prototypical work models, a search is implemented to determine which, of all the spectral state sequences of which the permitted word sequences are composed, presents the lowest dissimilarity score as compared with that of the spoken sentence.

In the case of continuous speech recognition featuring Markov word models, recognition consists in searching for the word model sequence having the highest probability that the spectral state sequence of the incoming voice signal has been emitted by the said models.

Using probability inverse logarithms instead of direct probabilities, the various probability terms relative to both the transition matrixes (when passing from one model state to another) and the emission matrixes (when emitting symbol from a model) may be added instead of multiplied, for calculating a probability score. Hence, the problem again amounts to searching fir the path minimizing a dissimilarity score.

A recognition process based on Markov word models is described, for example, in the article entitled "An introduction to hidden Markov models" by L. R. Rabiner and B. H. Juang, published in IEEE ASSP Magazine, January 1986.

In both cases, for crossing a sentence level network arc, i.e. the automaton representingg the permitted word sequences, the subnetwork representing the sequence of spectral states constituting the word in question must also be crossed. Both search levels are conducted by different processes, the sentence level process constituting the master level, and the other the slave level.

Substantially, the master process informs the slaves when a given path is to cross a given arc, and receives from the slaves data about the subnetwork output relative to the arc in question, i.e. the dissimilarity score of the path leaving the arc and the instant the path entered the arc. At each instant, the master then memories only the best path terminating on each master level network node.

Not all possible paths are subjected to a search in the grammar network. A pruning mechanism is implemented for gradually eliminating less probable paths, i.e. those having a higher dissimilarity score, in excess of a given predetermined threshold, than the best path detected up to the foregoing frame.

The recognition process must also taken into account the fact that each individual word may be pronounced at different speeds, thus giving rise to a varying number of spectral states. From the model comparison standpoint, this amounts to the possibility of certain spectral states appearing twice in slowly pronounced words, once in words pronounced at normal speed, or failing to appear at all in words pronounced quickly.

This is therefore taken into account by the comparison process at word level by providing for three types of transition within the acoustic subnetwork describing each individual word: repetition of a given state, normal forward transition to the next state, and skipping of a given state.

The search process for the best path within the grammar network, which, as already stated, is conducted at two hierarchical levels, master (sentence level search) and slave (word level search), makes use of dynamic programming operations.

Hereinafter, a dynamic programming operation OPD (ta) in frame ta is defined as the whole of the Na dynamic programming operations OPD (ta, na) over all the active arcs na ($1 \leq na \leq Na$) in the grammar network in frame ta.

Each OPD (ta, na) on arc na in frame ta is defined as the whole of the Sa dynamic programming operations OPD (ta, na, sa) over all the active states sa ($1 \leq sa \leq Sa$) of arc na.

An active arc na is a grammar network arc whose model contains at least one active state sa. The latter is a model state on which a likely path terminates at a given instant ta, i.e. a path having a dissimilarity score below the given threshold up to instant ta.

All the words known to the system are marked with a word index wi.

The OPD (ta) is performed at slave level.

At each frame, the master supplies the slave with acoustic parameters representing the spectral state of the acoustic signal to be identified in that particular frame, as well as a list of data relative to new grammar arcs na to be searched by the slave.

The slave processes the incoming data and supplies the master with a list of hypothesized terminated grammar arcs na, i.e. hypothesized word endings, together with a list of surviving arcs or paths, to enable the master to prune the abandoned paths from the grammar network.

The master level operations may be performed by a single processing unit, even in the case of complex grammar network structures, by virtue of computational complexity increasing only very slowly alongside an increase in the number of network nodes, particularly as a result of the said path pruning mechanism.

Computational complexity at slave level, on the other hand, increases in proportion to the number of words in the grammar network sentences. Hence, operation at slave level is preferably shared between a number of processing units, each charged with handling a given subset of words.

FIG. 1 shows a basic operation diagram of each slave level processing unit.

For performing an OPD (ta) operation, each slave unit uses the following storage areas:

area PAR into which, at each frame, newly detected acoustic parameters are entered by the master, together with other data such as the path pruning threshold value. The data stored in area PAR area is the same for all the slave units. Area PAR also comprises a table MAIL containing data exchanged between the master and each slave unit.

Area PUSH into which the master substantially enters data relative to the list of new grammar arcs na to be activated at each frame. Area PUSH contains specific data for each slave unit.

Area POP into which the slave unit enters data for the master unit relative to the list of grammar nodes terminated in each frame. Lists PUSH and/or POP need not necessarily appear at each frame.

Area BACK into which, at each frame, each slave unit enters data for the master unit relative to all the starting nodes of the surviving paths in the grammar network, for enabling the master to prune away any abandoned paths from the grammar network.

Area VOC for permanently storing data relative to the acoustic parameters of word subset models handled by each slave unit.

Work area LAV for storing and updating, at each frame, data relative to the states sa of active grammar arcs na.

The following is a detailed description of the content of the above storage areas.

Figure 2:
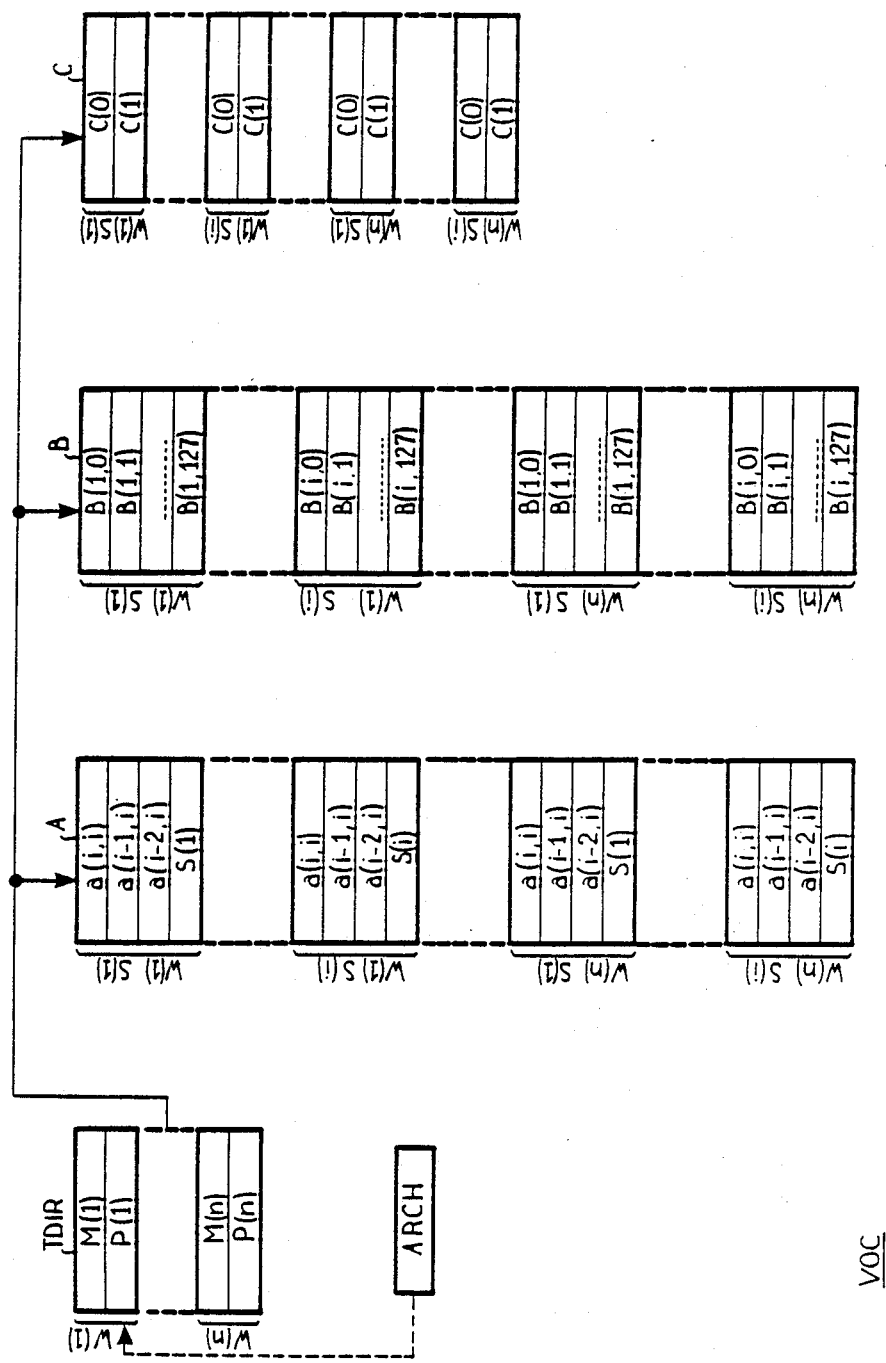
FIGS. 2, 3, 4 and 5 show the content of the various external memory tables.

FIG. 2 shows data organization inside storage area VOC, which comprises tables TDIR, A, B and C organized in blocks of a given number of words for each vocaculary word w(n).

For interpreting the data in the above tables, it is important to bear in mind that each individual word w(n) is represented as a sequence of states s(i) with $0 \leq i \leq I$. The states shown in A, B and C are therefore I+1 due to the existence of a dummy end state simulating the first state of the next word in the sentence.

The number of states I is a function of each individual word. Furthermore, in the course of recognition, each generic state s(i) may be reached from the same state s(i), from the foregoing state s(i-1), or from state s(i-2), with different probability values hereinafter referred to as the transition cost.

Addressing table TDIR is organized in two-word blocks for each vocabulary word w(n): in the first word, field M(n) indicates the number of states s(i) assigned to word w(n), and field P(n) the position of the first state in the block relative to the same word w(n) in tables A, B and C.

Table A is organized in four-word blocks for each state s(i) of each word w(n):

in the first word, field a(i,i) indicates the transition cost from state s(i) to the same state s(i). Values a in the table are determined only once at the node model definition stage. In the case of Markov models, Fields a present a quantity ($-\log P$), wherein P is the transition probability.

In the second word, field a(i-1, i) indicates the transition cost from state s(i-1) to state s(i).

In the third word, field a(i-2, i) indicates the transition cost from state s(i-2) to state s(i).

The fourth word is disregarded when using Markov models. In the case of prototypical models, field S(i) contains the index of the spectral vector codebook symbol representing the word state s(i).

Table B is only used for Markov models and, for each state s(i) of each word w(n), contains the inverse of the logarithm of the emissionprobabilities B(i, 0), . . . B(i, 127) relative to all the spectral vector codebook symbols, i.e. the probabilities of the index of the spectral codebook symbol (0 . . . 127) being emitted in state s(i) of W(n).

Codebook symbol number may be 128 or 256.

Table C is only used for Markov models and, for each state s(i) of each word w(n), contains the inverse of the logarithm of the emission probabilities C(0), C(1) relative to a high and low energy state respectively, i.e. the probabilities of a high or low energy value being detected in state s(i).

The content of tables TDIR, A, B and C are loaded only once by the master into area VOC area at the system initialization stage, and are then only read in normal operating mode.

Reading in VOC is performed via field ARCH containing the code of word w(n) for addressing table TDIR which, in turn, contains data for addressing tables A, B and C.

Tables A, B and C are addressed according to the following equations:

$$INDA = AIN + CLA \cdot [P(n) + IS(i)]$$

$$INDB = BIN + CLB \cdot [P(n) + IS(i)]$$

$$INDC = CIN + CLC \cdot [P(n) + IS(i)].$$

INDA, INDB, INDC are the actual addresses for access to tables A, B and C respectively at the i-th state of the n-th word; AIN, BIN, CIN are the actual starting addresses of tables A, B, and C; CLA, CLB, CLC represent the number of words per block in each table (in the example shown, CLA=4, CLB=128 or 256, CLC=2); IS(i) is the state index of word w(n); P(n), obtained from table TDIR, represents the total number of states of all the words memorized with the progressive indices in the tables up to word w(n−1), according to the equation:

$$P(n) = \sum_{j=0}^{n-1} [M(j) + 1]$$

wherein the 1 is added to account for the dummy end state stored in the memory for each word w(n).

Thus, using the same indices P(n), IS(i), all three tables A, B and C may be addressed separately by simply modifying constant values AIN, . . ., CLC.

Figure 3:
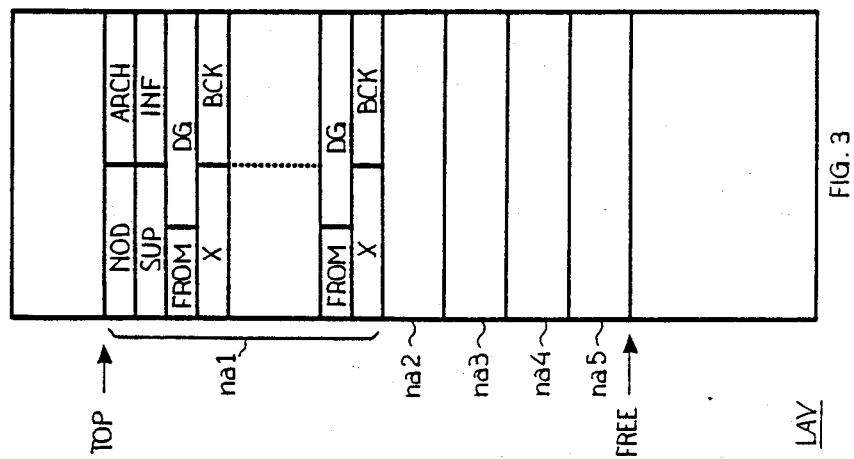

FIG. 3 shows data organization inside storage area LAV.

At each frame ta, area LAV contains data relative to the states sa of active arcs na.

Area LAV is divided into blocks (five in the example shown: na1 . . . na5) each containing data relative to the states of an active arc, i.e. to an operation OPD (ta, na). The said data is, in turn, divided into fields as shown for arc na1 in FIG. 3.

The first two words form the heading and comprise fields NOD, ARCH, SUP and INF.

Fields ARCH and NOD contain the index of the word and its context within the grammar network, whereas fields INF and SUP contain the index of the first and last state in the state sequence of the respective arc (na1) which were found to be active in the foregoing frame. These values generally change at each frame.

The heading is followed by word pairs, one for each state, comprising fields FROM, DG and BCK. The fields marked X are not used.

The pertinent states are those having indices ranging between INF−1 and SUP+2, the upper limit consisting of the actual end state (index M(n)−1) of the word.

In other words, for each active arc na, area LAV memorizes, not the whole model but only the model state segment which is active at each frame.

Field DG contains the cumulative distance (or transition cost) value for reaching that particular state along the lowest cumulative distance path in the search process. In the case of Markov models, the cumulative distance is the sum of the inverses of the logarithms of cumulative emission and transition probabilities.

Field FROM provides for coding the immediate origin of the best path, i.e. from which state in arc na state sa was reached at frame ta−1, according to the following possibilities:
best path in ta, na, sa is from ta−1, na, sa;
from ta−1, na, sa−1;
from ta−1, na, sa−2;
state ta, na, sa is inactive, i.e. no valid path below the given threshold arrives at it (in which case, fields FROM and DG are coded with logic levels 1 only).

Field BCK contains the master-supplied code of the source grammar node and frame of the best path through ta, na, sa.

Area LAV is managed cyclically by means of two pointing addresses (TOP and FREE in FIG. 3) relating respectively to the first word in the block relative to the arc to be processed, and the first free line.

Block indicated by TOP is read, updated by operation OD (ta, na), and rewritten commencing from point FREE in the free area.

TOP and FREE are then shifted to find the next block to be processed and the next free area.

Figure 4:
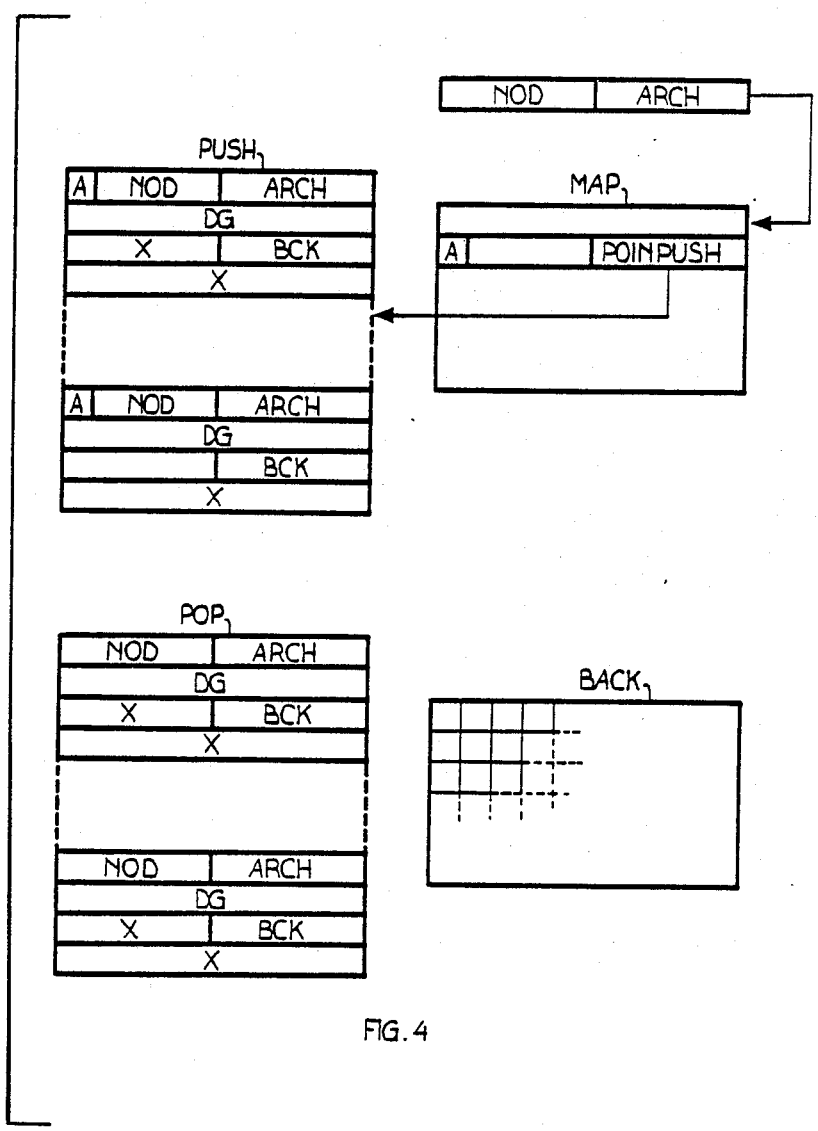

FIG. 4 shows data organization inside storage areas PUSH, POP and BACK and an additional area MAP.

Areas PUSH and POP contain four-word blocks for each arc na.

Fields NOD, ARCH, DG and BCK of each block are as already described in connection with the blocks in area LAV in FIG. 3.

The blocks in area POP relate to grammar nodes recognized in the current frame (dynamic programming successfully reaching the last state) and which have been written by the slave and read by the master, which, in the next frame, accordingly supplies a table of area PUSH containing data relative to all the arcs in the grammar network departing from the nodes on which the arcs in area POP terminate.

The algorithm implementing OPD (ta) provides for reading the blocks in area PUSH both singly and sequentially, the blocks read once being marked by field A which, after the first reading, is set to an appropriate identification logic level.

For addressing individual blocks in area PUSH, provision is made for a table MAP, which is written and read only by the slave. At the address in MAP defined by fields NOD and ARCH of each block in area an index or order number POINPUSH of the block in list PUSH is written.

Area BACK is structured in the form of a map, each location of which corresponds with one of the 256 coding employed by the master for determining the grammar nodes and the various path starting points.

The logic level of each location acts as a code for indicating the existence or nonexistence, among all the active arcs na in a given frame, of at least one active state having a code BCK corresponding with that particular location.

At the end of an OPD (ta), the said map enables the master to prune the paths in the hypothesized word sequence subnetwork being constructed.

Figure 5:
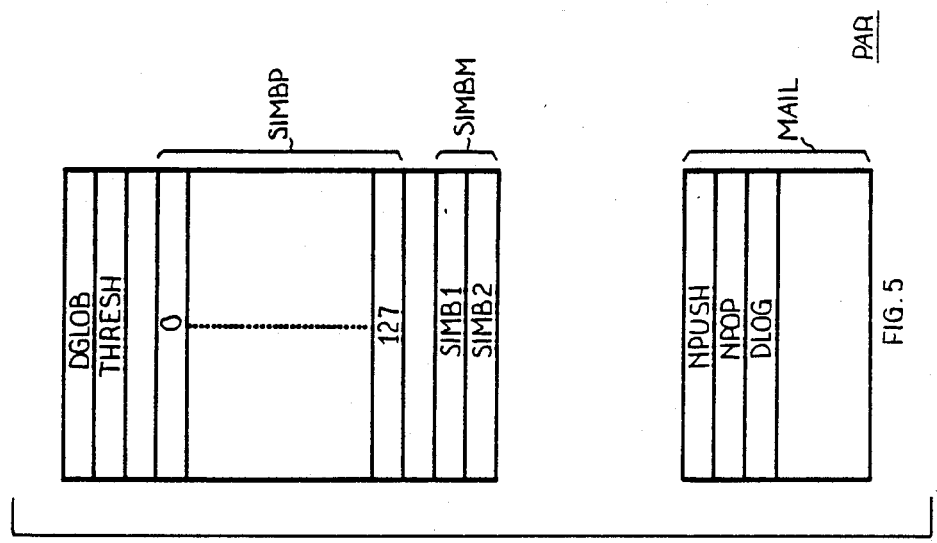

FIG. 5 shows data organization inside the PAR storage area.

Field DGLOB contains the best total distance value in the foregoing frame supplied by the master at each frame and selected from among distances DLOC supplied by individual slaves.

Field THRESH contains the path pruning threshold value, which is supplied by the master at each frame.

Fields SIMBP and SIMBM s contain codes relative to the acoustic parameters in the latest frame for prototypical and Markov models respectively.

SIMBP contains the distance values of acoustic parameters detected with respect to each of the coded vectors.

SIMBM contains two words: SIMB1, which is the spectral code index in the codebook; and SIMB2, which is the index of one of the two possible energy levels relative to the latest acoustic parameters.

Area MAIL is a table containing additional information exchanged between the master and slave. Field NPUSH is written by the master and contains the number of blocks in area PUSH at each frame. Field NPOP is written by the slave and contains the number of blocks in area POP at each frame. Field DLOC is written by the slave and contains the best local distance value at each frame as calculated by the slave.

The remaining portion contains information which is a replica of an internal holding area of the slave and of possible use to the master.

The dynamic programming operation OPD (ta) performed at each frame will now be described with reference to the main flow chart in FIG. 6, and flow charts in FIGS. 7 and 8 which show more detailed operation of a number of blocks in FIG. 6.

Figure 6:
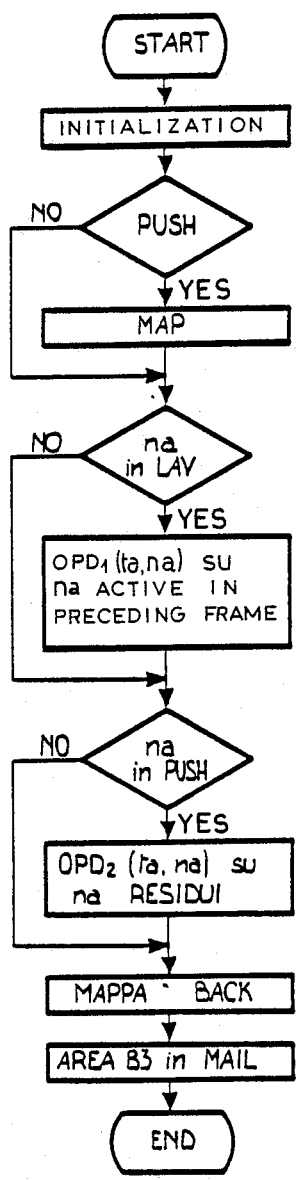
FIGS. 6, 7 and 8 show flow charts of the connected speech recognition microprogram.

As shown in FIG. 6, at the START of each frame, an initialization operation is performed, which consists in copying from the external memory into internal memory bank B3 filed DGLOB, THRESH, SIMB1 and SIMB2 from area PAR, and field NPUSH from area MAIL. If area PUSH is not empty, this is read sequentially for preparing table MAP as already described in connection with FIG. 4.

Address TOP in area LAV is then addressed for commencing dynamic programming OPD (ta, na) on the arcs active in the foregoing frame. If there were no active arcs in the foregoing frame (e.g. at the start of programming), this part of the chart is obviously skipped, as though the area LAV were empty.

Figure 7:
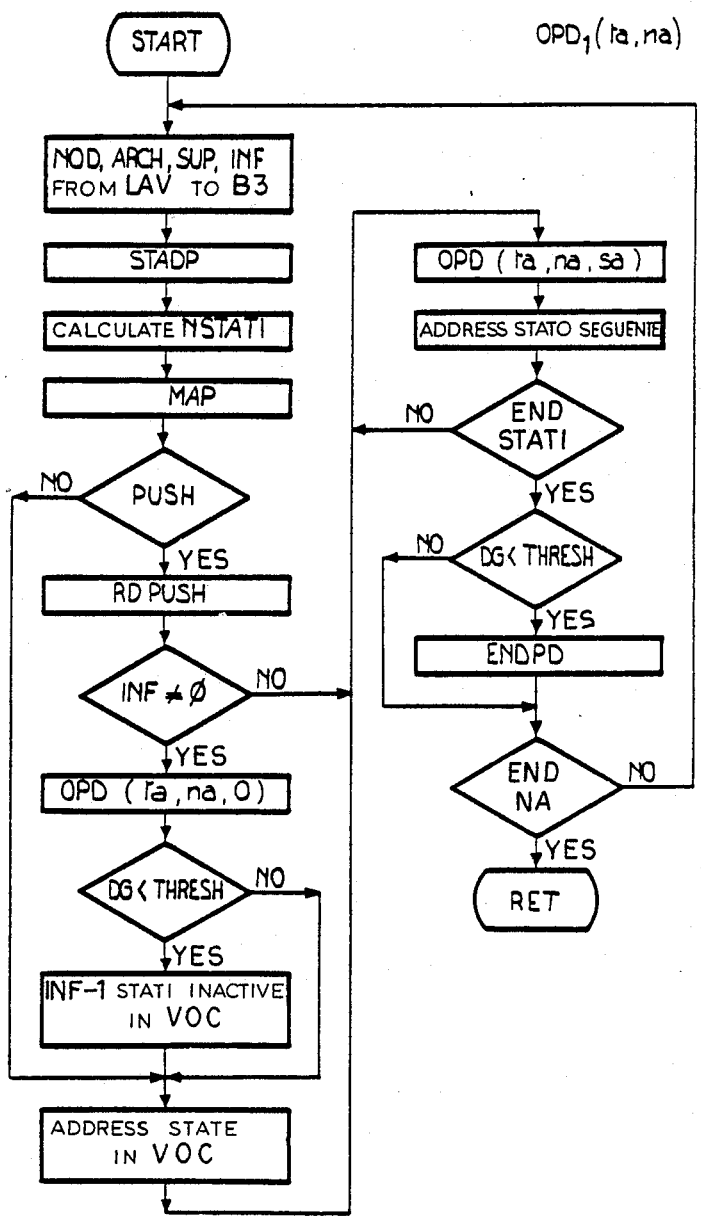

The relative operation sequence is detailed in FIG. 7 to which the following description refers.

The first active arc heading (fields NOD, ARCH, SUP, INF) is read in area LAV and copied into bank B3.

The following operations are then performed in starting subroutine STADP of dynamic programming on the said arc: banks B0 and B1 are initialized with two inactive states with indices INF-1 and INF-2, and the area in LAV addressed by FREE and subsequently containing the updated acoustic description of the said arc is initialized with an inactive state INF-1. For coding an inactive state, the relative fields FROM and DG are assigned a logic "1".

Values NOD and ARCH provide for determining values M(n) and P(n) of the active arc in table TDIR of area VOC, and for subsequently addressing, in tables A, B AND C, data relative to the first state (state 0) of the arc by compiling the addresses as described in connection with FIG. 2.

NSTATI, i.e. the number of states of the active arc being updated, is then calculated as:

$$NSTATI = \overline{min[SUP+3,M(n)] - INF}$$

and the resulting value entered into B3.

Table MAP (FIG. 4) is then addressed with said values NOD and ARCH. If the addressed value does not correspond with an arc in list PUSH, the acoustic description of state INF is addressed in area VOC.

If, on the other hand, the addressed value is found to correspond with an arc in the PUSH list, subroutine RDPUSH is performed: fields DG and BCK in table PUSH table are read and copied into banks B0 and B1 at state −2 (relative to state 0 of the node addressed in PUSH). Field A in the PUSH and MAP tables is then marked, and an inactive state entered into B0 at index −1.

If INF=0, inactive state INF-1 state is addressed in LAV, and an operation OPD (ta, na, 0) operation performed relative to the 0 state. If the calculated cumulative distance DG is found to be below threshold thresh, inactive states 1 to INF-1 are entered in LAV, for read-addressing the acoustic description of state INF in VOC.

Figure 8:
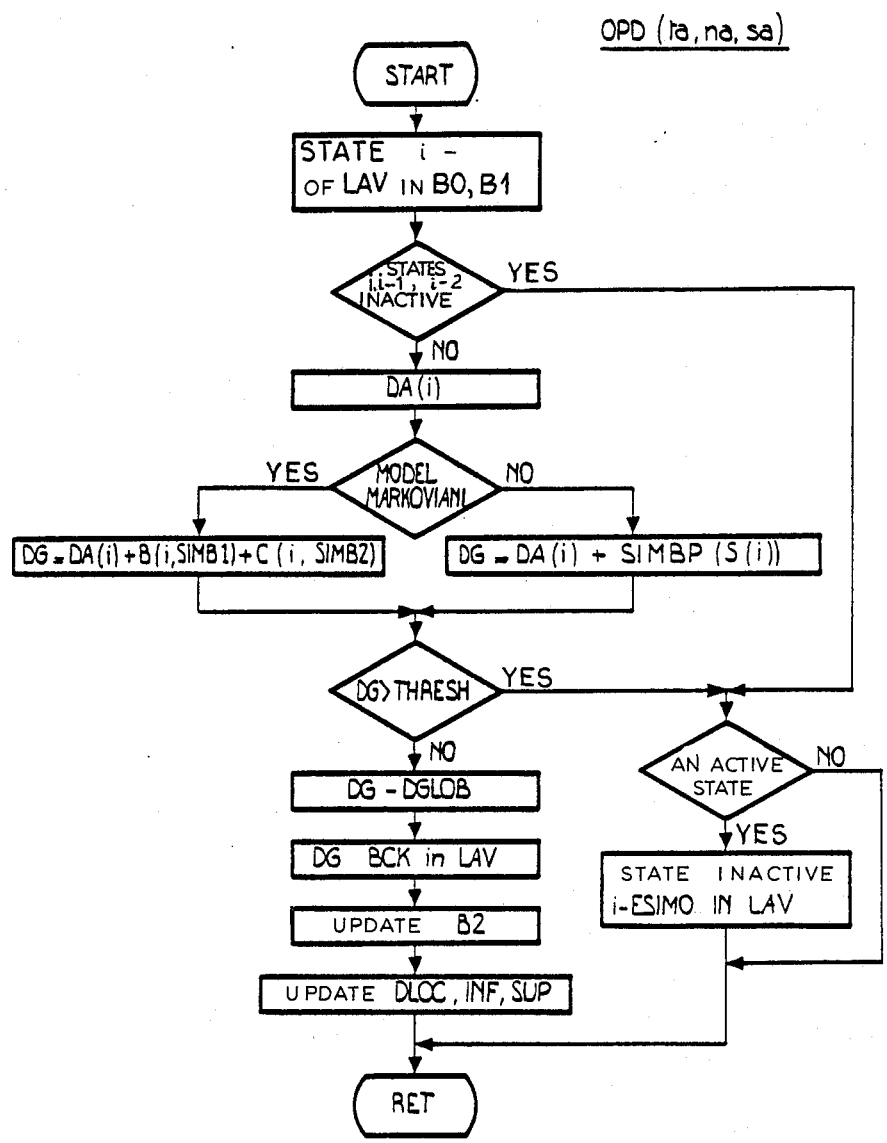

Dynamic programming subroutine OPD (ta, na, sa) is then performed on an active state, with sa initially equal to INF, and the flow chart of which is shown in FIG. 8 to which the following description refers. The said operations are also those performed for state 0 referred to above.

The data in LAV relative to the i-th state to be updated is read and entered into banks B0 and B1. The first state read on entering the subroutine presents index INF.

If at least one of states i, i-1 and i-2 now read in B0 and B1 is active, the following computations are carried out on the said states.

Value DA(i) is calculated as:

$$DA(i) = min[DG(i=j) + a(i-j,i)]$$
$$j = 0,1,2$$

wherein DG(i−j) is the cumulative distance at state (i−j) in B0, and a(i−j,i) is one of the values read in table A of VOC relative to the i-th state.

In the case of Markov models, the following operation is performed:

$$DG(i) = DA(i) + B(i,SIMB1) + C(i,SIMB2)$$

wherein DG(i) is the latest cumulative distance value relative to the i-th state. Values B(i,SIMB1) and C(i,-SIMB2) are read in tables B and C of VOC in the i-th state of that particular node, at the relative addresses SIMB1 and SIMB2 read in bank B3.

In the case of prototypical models, the following operation is performed:

$$DG(i) = DA(i) + SIMBP(S(i))$$

wherein SIMBP(S(i)) is the value read in table PAR in area SIMBP, at the relative address S(i) read in table A in the i-th state.

If the latest value DG(i) is over threshold thresh read in B3, and states i, i-1 and i-2 are found to be inactive in the previous comparison, the i-th inactive state is entered into LAV if the cumulative distance DG of at least one state has been previously found to be below the threshold, thus terminating subroutine OPD (ta, na, sa).

If, on the other hand, the latest cumulative distance DG is found to be below threshold thresh, value DGLOB is subtracted from the latest value DG; the resulting value DG and value BCK, corresponding to the best local path just found, are entered into LAV at the i-th state; the location corresponding to the latest value BCK is marked on the map in B2; and the following fields are updated in bank B3; DLOC, as the minumum of the value in B3 or the latest DG value decremented by DGLOB; SUP, which is equalled to i; and INF, which is also equalled to i if the i-th state is the first active state in the arc.

The subroutine is thus terminated and sequence of FIG. 7 is resumed.

The subroutine OPD (ta, na, sa) is repeated NSTATI times. At each new state, the next state is read- and write-addressed in areas LAV and VOC area and blocks B0 and B1.

Once all the states have been terminated, area LAV will contain the updated situation of the active arc starting from address FREE.

Consequently, if, for at least one of the states examined, DG is found to be below threshold thresh, the arc remains active and subroutine ENDPD is performed whereby: a one-unit increment is made to an active arc counter counter SURV in B3, which is reset at the start of each frame; two inactive states SUP+1 and SUP+2 are entered into LAV as the last two states of the active arc in question; and fields NOD, ARCH, SUP and INF in LAV are updated with the values in B3: values NOD and ARCH are those read at the start of the sequence OPD (ta, na), whereas INF and SUP are usually changed.

A check is then made to determine whether $M(n) - 2 \leq SUP$. If it is, recognition of the arc is assumed to be terminated and the following operation is performed:

$$DA = \min\{DG[M(n)-j] + a[M(n)-j, M(n)]\}$$
$$j = 1, 2$$

wherein the state with index $M(n)$ is the dummy end state.

An increment is then made to a terminated arc counter NPOP counter in B3, which is reset at the start of each frame. The terminated arc fields NOD and ARCH, the above value DA in field DG, and value BCK relative to the selected minimum are then copied into area POP.

The new address FREE (Na+1) in area LAV is calculated as:

$$FREE(Na+1) = FREE(Na) + \min[SUP+5, M(n)+2] - INF$$

which marks the end of subroutine ENDPD.

If there are still active arcs for processing, operations $OPD_1$ (ta, na) in FIG. 7 are repeated relative to the next arc in LAV. If not, the main sequence in FIG. 6 is taken up again, which now provides for analyzing tables PUSH to determine whether there are any arcs that have not yet been analysed, i.e. which did not appear in area LAV in the foregoing frame. These are the arcs having field A as yet unmarked and on which the following operations $OPD_2$ (ta, na) are performed.

The entire table PUSH is reread and the arcs marked in field A disregarded. For any others as yet unmarked, field A is marked in the table MAP and subroutines STADP, RDPUSH and OPD (ta, na, 0) already described are performed. If the resulting distance DG(0) relative to state 0 is still below the threshold, subroutine ENDPD already described is performed, after which, the next arc in area PUSH area is processed, and so on until all the arcs have been processed.

Once all the arcs in list PUSH have been processed, a number of closing operations are performed: map BACK is copied from bank B2 into the external memory area in FIG. 6, and the parameters in area B3 are copied into the MAIL area.

This marks the end of the slave function within a given frame.

Dynamic programming operations OPD(ta) are performed by one or more components featuring very large-scale-integration CMOS integrated circuits.

Each integrated circuit functions as a slave within the two-level hierarchical structure.

Figure 9:
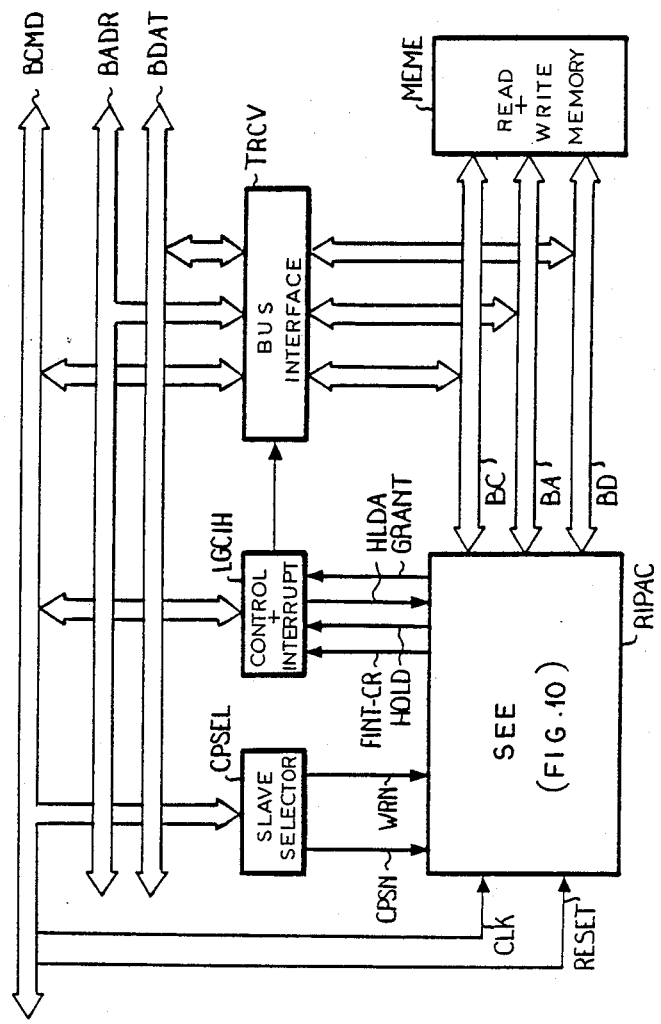
FIG. 9 shows the manner in which the circuit according to the present invention is incorporated within a two-level hierarchical system.

FIG. 9 shows a connecting diagram of one of the said components, denoted by RIPAC, in the system.

BCMD, BADR and BDAT indicate the control, address and data buses, respectively, of the master level (not shown) to which one or more components RIPAC are connected.

MEME indicates a read and write memory containing areas PAR, PUSH, POP, BACK, LAV and VOC already discussed. MEME may be written in and read by both component RIPAC and the master via local buses BC (control bus), BA (address bus) and BD (data bus).

CPSEL indicates a block enabling in known manner slave selection by the master. The said block CPSEL identifies, on bus BCMD, the bit configuration by which the respective slave is known to the master, and generates and supplies selection and write signals CPSN and WRN to component RIPAC.

LGCIH indicates a known block for handling known external bus control signals and interrupt signals (INT, HOLD, HLDA, GRANT) exchanged with the RIPAC component.

LGCIH exchanges the control signals with the master via bus BCMD. Signals HOLD, HLDA and GRANT provide for mutually exclusive access to memory MEME by either RIPAC or the master. Memory MEME is normally connected to component RIPAC which, in given release time intervals, issues a GRANT signal. For enabling master access to memory MEME, when the GRANT signal is supplied, the master takes over the control at the internal RIPAC buses by exchanging signals HOLD, HLDA and GRANT via block LGCIH, which also controls a known block TRCV for two-way connection of the master buses and internal RIPAC buses.

The following description relative to external connections, of component RIPAC is sufficient to enable a technician skilled in the art to design circuits CPSEL, LGCIH and TRCV. The structure of block RIPAC, on the other hand, to which the present invention relates, is as shown in the overall block diagram in FIG. 10.

Figure 10:
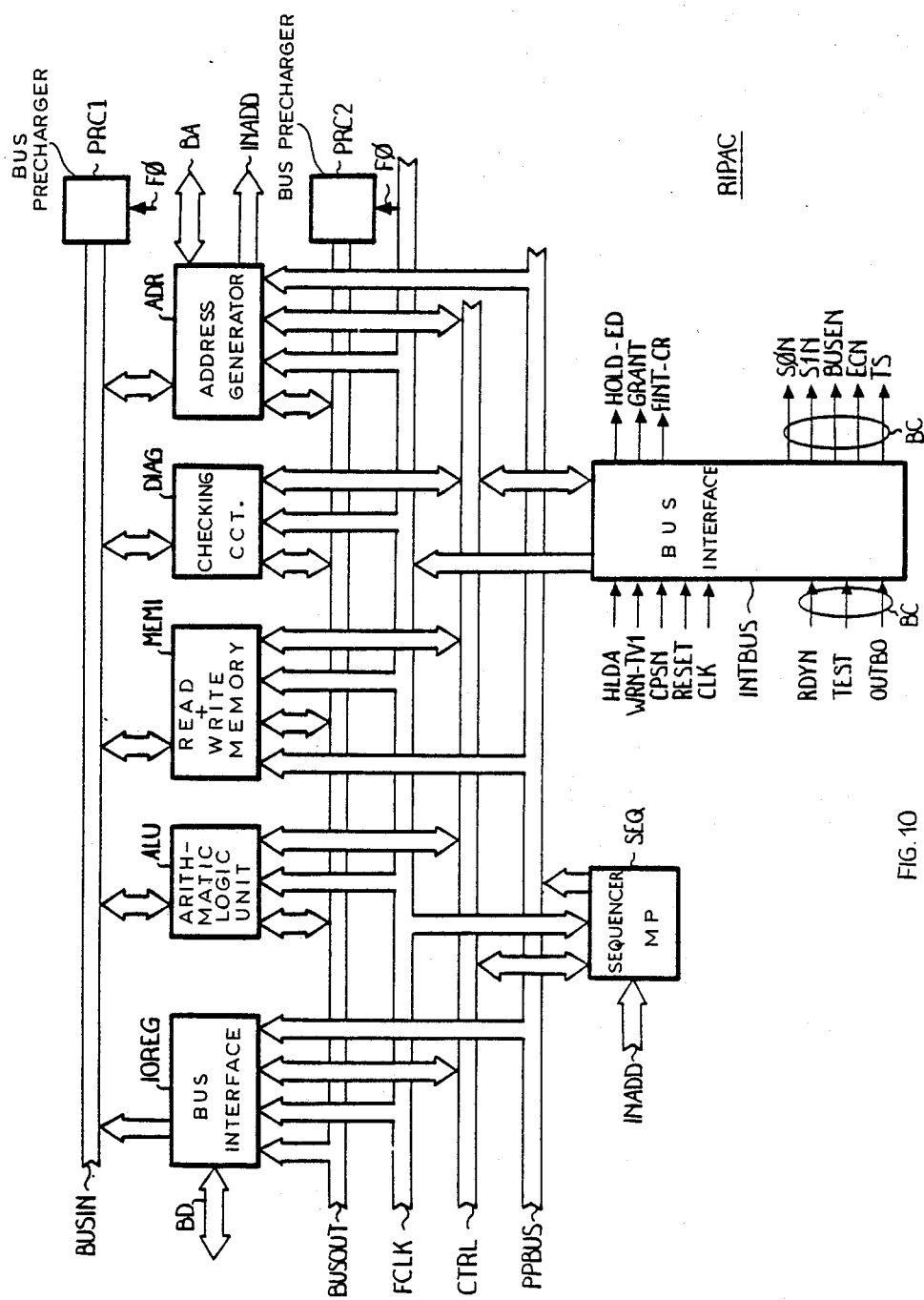
FIG. 10 shows a major block diagram of the circuit.

INTBUS in FIG. 10 indicates a block predominantly acting as bus interface, i.e. controlling two-way dialogue between the component and external buses, for example, as specified in the INTEL "iAPX 286 Hardware Reference Manual".

INTBUS received selection signals CPSN and WRN-TV1 from block CPSEL (FIG. 9), and a signal HLDA from block LGCIH, and generates return signals HOLD-ED and GRANT for the LGCIH block, and external bus control signals SON, SIN and BUSEN which are carried on bus BC (FIG. 9) over which INTBUS is supplied a signal RDYN by the external memory MEME. Test signals TEST, OUTBO, ECN and TS are exchanged between INTBUS and the master via bus BC.

INTBUS also exchanges internal control signals on bus CRTL, for controlling data input/output operations on external buses BD and BA.

INTBUS also provides for a further two functions: controlling internal reset signals which it generates according to a signal RESET coming from the master (FIG. 9); and generating a four-phase internal clock signal, supplied on bus FCLK, according to a clock signal CLK also coming from the master (FIG. 8). Bus FCLK is connected to all circuit blocks in FIG. 10.

One embodiment of block INTBUS will be described with reference to FIG. 11.

SEQ indicates a microprogram sequencing block providing for the following sequencing modes:
normal mode: by incrementing a microprogram counter;
conditional or unconditional branch to a subroutine;
conditional or unconditional subroutine call;
conditional or unconditional return from a subroutine.

An external starting address may be forced into SEQ, which address is switched by INTBUS from BA to input bus INADD of SEQ. This is how dynamic programming at each frame, as well as random test procedures described in more detail later on, are usually started.

SEQ also comprises a stack register for temporarily storing one or two main program re-entry point addresses, and so providing for two subroutine nesting levels.

SEQ comprises registers for temporary microinstruction storage, said registers being controlled by the known "pipeline" technique enabling overlapping performance of one microinstruction and access to the next, as described in more detail later on. SEQ supplies the microinstruction fields present in more than one cycle and those varying at each cycle over buses PPBUS and CTRL buses respectively, and receives control signals from block INTBUS.

A detailed description of the structure of block SEQ will be given with reference to FIG. 12.

Block IOREG mainly provides for connecting the two-way bus BD to two known precharge internal buses: data input bus BUSIN and data output bus BUSOUT.

BUSIN and BUSOUT are precharged by means of two known circuits, PRC1 and PRC2, which, during phase FO extracted from bus FCLK, "precharge" the said buses with a logic level "1". Enabling circuits in the blocks connected to BUSIN and BUSOUT provide for writing on the said buses by forcing logic levels "0" wherever necessary.

Via a control signal from INTBUS on bus CTRL, IOREG may transfer the content of BUSOUT onto BD, or that of BD onto BUSIN.

IOREG also provides for three further functions, controlled by signals coming from the sequencer signals on buses CTRL and PPBUS: transferring first the least significant part and then the most significant part of BD into the least significant part of BUSIN, in two successive microinstruction cycles, by setting the most significant part of BUSIN to logic level "0"; transferring the content of BUSIN to BUSOUT or vice versa; trasferring the most or least significant part of BUSOUT to the most significant part of BUSIN.

A detailed description of the structure of block IOREG will be given with reference to FIG. 13.

Block ADR provides for generating external memory read and write addresses, and comprises two internal read and write memories MEMIN and MEMOF.

MEMIN contains the starting addresses MEMIN(i) of the external memory tables in FIGS. 2, 3, 4 and 5, which are compiled only once at the initialization stage.

MEMOF provides for temporarily storing the addresses of four word block locations MEMOF(j) in the external memory tables, with respect to the start locations of the tables, the said word blocks being those used for each of the said dynamic programming operations. In certain microprogram stages, for example, MEMOF contains the LAV area pointers TOP and FREE.

The generic external memory address ADRE is calculated by ADR according to the following equation:

$$ADRE = \{2^{16+W} \cdot MEMIN_H(i) + 2^W \cdot [MEMIN_L(i) + MEMOF(j)]_{module-216} + +DISPA \mid_{module-2W}\}_{module-223}$$

wherein: module-$2^{23}$ indicates that 23 is the maximum number of address bits; $2^W$ is the maximum number of words in a record within which value DISPA, which has W bits, indicates the individual word; MEMOF(j) indicates the order number of the record in the table; $MEMIN_L$ (i) is the portion of MEMIN(i) relative to the 16 least significant bits, and $MEMIN_H$(i) the portion relative to the remaining 7 most significant bits.

Given the above compositions of address ADRE, the format of each individual record clearly also governs the actual starting address of the table containing the record, in the sense that a table consisting of records of N words can only start from addresses dividable by N.

ADR supplies addresses on bus BA, enabled by INTBUS over bus CTRL, and receives addresses for storage in memories MEMIN and MEMOF from bus BD via bus BUSIN.

A detailed description of the structure of block ADR will be given with reference to FIG. 15.

Block ALU functions as an arithmetical-logic unit, which receives an operand A from BUSIN and an operand B from BUSOUT for performing the following operations: A+B; A−B; comparing item A with threshold B; minimum of A and B; the operation results may be supplied on BUSIN or BUSOUT. The above operations are substantially used for calculating and updating distances DG.

A detailed description of the structure of block ALU will be given with reference to FIG. 16.

Block MEMI comprises an internal read and write memory RAMI and a logic circuit for generating access addresses to the said memory.

Write data is received over BUSIN and read data supplied over BUSOUT.

Functionally, the internal memory is organized in four banks, B0, B1, B2, B3, each with a capacity of sixteen 16-bit words.

Banks B0 and B1 share data relative to the last 16 states read in the external memory area LAV (FIG. 3). More precisely, bank B0 stores fields FRM and DG, and bank B1 field BCK. These two banks are organized cyclically, as suited to local dynamic programming operation performance.

Map BACK is constructed at each frame in bank B2 and copied into the homonymous external memory area (FIG. 4) at the end of each frame.

At the start of each frame, bank B2 is in the fully reset condition; it requires a specific bit addressing as well as the standard word addressing.

Bank B3 bank contains a number of working variables for performance of operations OPD (ta).

At the end of each frame, the content of bank B3 is copied into area MAIL.

A detailed description of the structure of block MEMI will be given with reference to FIG. 17.

DIAG is a circuit for checking the results of internal test procedures, and checks of overflow of area LAV, and processing overload.

The said results may produce in case of alarm an interrupt request FINT signal towards interface INTBUS, which generates signal FINT-CR supplied to the master via block LGCIH (FIG. 9).

Figure 14:
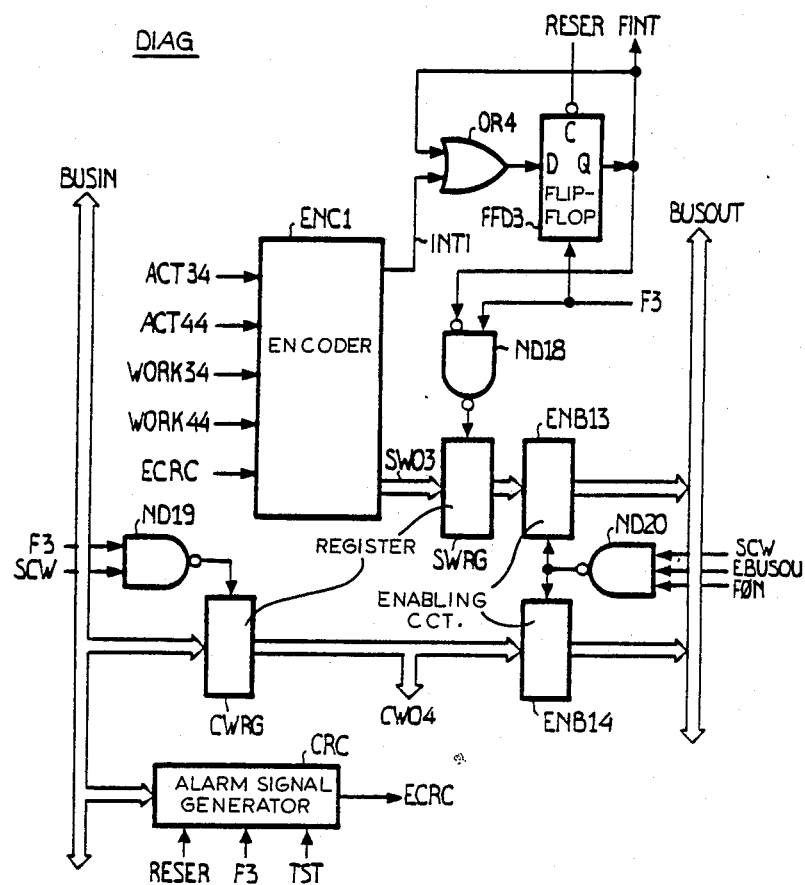
FIG. 14 shows a circuit diagram of block DIAG in FIG. 10.

A detailed description of the structure and operation of block DIAG will be given with reference to FIG. 14.

PLA1 in FIG. 10 is a finite state machine consisting of what is known as a PLA (programmable Logic Array).

Machines like PLA1 usually consist of an array of two planes of ANd and OR gates, with appropriate input-output feedbacks for producing a given number of states. The delay times introduced by such machines generally depend on how complex they are in terms of the number of product terms involved in the truth table being implemented.

In the present case, to reduce the number of product terms involved, provision has been made for four intermediate outputs, CR, ED, TS, ECN, to an additional logic circuit LGC1: PLA1 is thus a faster, 20-state machine with 33 product terms, clockable directly by a 16 MHz signal CLK, and LGC1 generages a number of signals which otherwise had to be generated by PLA1.

The inputs and outputs of PLA1 are clocked by opposite logic levels of CLK and the state signals are reset directly by a RESET signal which is not an input of PLA1.

PLA1 represents the following input signals:
EXT0,EXT1: from bus CTRL of sequencer SEQ (FIG. 12). These are also supplied to LGC1 and indicate one of the following external bus read/write cycle requests: no cycle, external memory writing, external memory reading, end of operation. The actual input to PLA1 consists of the ogic EX-OR of these two signals performed by gate EX1, the EXT2 output of which indicates the two read/write and end/no cycle conditions. In test mode, in place of output of EX1, PLA1 is supplied a WRN-TV1 signal via multiplexer MX1, controlled by a test mode enabling signal TEST. Output V of Mx1 is the actual input of PLA1;
HLDA: from block CPSEL (FIG. 9) and indicating a "hold acknowledge" condition;
RDYN: from controller of external memory MEME (FIG. 9) and indicating a data ready condition.

In addition to EXT0, EXT1, CR, ED, TS and ECN, LGC1 also presents the following input signals:
TEST: external test mode enabling signal;
FINT: generated by the diagnostic logic circuit DIAG (FIG. 14) and indicating an interrupt condition subsequent to an error;
OUTBO: only enabled in test mode, for reading the content of BUSOUT (FIG. 13) directly on bus BD (FIG. 9);
EXT2: output of circuit EX1;
WRN-TV1, CPSN: from circuit CPSEL (FIG. 9).

In normal operating mode, signal WRN-TV1, together with CPSN, provides for enabling component RIPAC. In test mode, it is supplied as an input to PLA1.
The output signals of PLA1 are:
WN: wait signal for suspending component operation until the external buses are made again available.
GRANT: external bus protocol signal.
BUSEN: enabling signal for external data exchange between buses BA, INADD and ADRE (FIG. 15).
TS, ECN: out-going test signals, also supplied to LGC1, together with signals CR and ED.
The LGC1 output signals are:
EDOUT, LRIN, LROUT: enabling signals for data exchange between BUSIN, BUSOUT and BD. In test mode, signal EDOUT (FIG. 13) is enabled subsequent to enabling of signal OUTBO.
SON, SIN: external bus state signals.
FINT-CR: in normal operating mode, this coincides with signal FINT generated by diagnostic logic circuit DIAG (FIG. 14). In test mode, it provides for making output CR of PLA1, which is otherwise unused, available outside component RIPAC (FIG. 10).
START: component start signal, for forcing an address into sequencer SEQ (FIG. 12) from the outside.
HOLD-ED: in normal operating mode, this indicates a "hold" condition and, toether with signals HLDA and GRANT provides for external bus control. In test mode, it provides for making output ED of PLA1 available outside component RIPAC.
WRIN: for controlling the first data input operation from bus BD, and involving internal reset via signal RESER.
ALE: supplid to sequencer SEQ (FIG. 12) for external address input control.

The circuits of INTBUS discussed so far perform known functions: also the meaning and timing of the relative input and output signals, as described in the aforementioned "iAPX 286 Hardware Reference Maual", are substantially known.

By way of an exemplary embodiment of block PLA1, the following is a truth table of inputs and outputs, together with present and future state signals $ST_p$, $ST_f$:

| HLDA | RDYN | V | $ST_p$ | $ST_f$ | BUSEN | CR | ECN | ED | GRANT | TS | WN |
|---|---|---|---|---|---|---|---|---|---|---|---|
| X | X | X | X1110 | 11111 | 1 | 0 | 0 | 0 | 0 | 0 | 0 |
| X | X | X | X0110 | 11100 | 1 | 0 | 1 | 1 | 0 | 0 | 0 |
| X | X | X | 110X0 | 11011 | 1 | 1 | 0 | 0 | 0 | 0 | 1 |
| X | X | X | 0X010 | 11000 | 0 | 0 | 1 | 1 | 1 | 0 | 0 |
| X | X | X | 11X00 | 10111 | 1 | 0 | 0 | 0 | 0 | 0 | 1 |
| X | X | X | 0X100 | 10100 | 1 | 1 | 1 | 1 | 0 | 0 | 1 |
| X | X | X | 100X0 | 10001 | 1 | 1 | 1 | 1 | 0 | 0 | 1 |
| X | X | X | 0X000 | 10000 | 0 | 1 | 1 | 1 | 1 | 0 | 1 |
| X | X | X | 101X0 | 00001 | 0 | 0 | 0 | 0 | 0 | 1 | 1 |
| X | 1 | X | X111X | 01111 | 1 | 0 | 0 | 0 | 0 | 0 | 0 |
| X | 1 | 1 | X1XX1 | 01111 | 1 | 0 | 0 | 0 | 0 | 0 | 0 |
| X | 0 | 1 | X1XX1 | 01101 | 1 | 0 | 1 | 1 | 0 | 1 | 1 |
| X | X | X | 0X111 | 01101 | 1 | 0 | 1 | 1 | 0 | 1 | 1 |
| X | 0 | X | X1111 | 01101 | 1 | 0 | 1 | 1 | 0 | 1 | 1 |
| X | X | X | 0XX11 | 01100 | 0 | 0 | 1 | 1 | 0 | 0 | 0 |
| 1 | X | 1 | X0X01 | 01100 | 0 | 0 | 1 | 1 | 0 | 0 | 0 |
| X | X | X | 101X1 | 01011 | 1 | 1 | 0 | 0 | 0 | 0 | 1 |
| 0 | X | 1 | 0X101 | 01010 | 0 | 0 | 1 | 1 | 0 | 0 | 0 |
| 0 | X | 1 | 1X001 | 01010 | 0 | 0 | 1 | 1 | 0 | 0 | 0 |
| 0 | X | X | 0X01X | 01000 | 0 | 0 | 1 | 1 | 1 | 0 | 0 |
| 0 | X | 1 | 0X0X1 | 01000 | 0 | 0 | 1 | 1 | 1 | 0 | 0 |
| 1 | X | 1 | 0X1X1 | 00001 | 1 | 0 | 0 | 0 | 0 | 1 | 1 |
| 1 | X | 1 | 100X1 | 00001 | 1 | 0 | 0 | 0 | 0 | 1 | 1 |
| X | 1 | 0 | X10X1 | 00111 | 1 | 0 | 0 | 0 | 0 | 0 | 1 |
| X | 1 | 0 | 1X10X | 00111 | 1 | 0 | 0 | 0 | 0 | 0 | 1 |
| 1 | X | 0 | 0X001 | 00100 | 0 | 1 | 1 | 1 | 0 | 0 | 1 |
| 0 | X | 0 | 0X101 | 00010 | 0 | 1 | 1 | 1 | 0 | 0 | 1 |

-continued

| HLDA | RDYN | V | ST$_p$ | ST$_f$ | BUSEN | CR | ECN | ED | GRANT | TS | WN |
|---|---|---|---|---|---|---|---|---|---|---|---|
| 0 | X | 0 | 1X001 | 00010 | 0 | 1 | 1 | 1 | 0 | 0 | 1 |
| X | 0 | 0 | X10X1 | 00001 | 1 | 1 | 1 | 1 | 0 | 0 | 1 |
| 1 | X | 0 | 0X101 | 00001 | 1 | 1 | 1 | 1 | 0 | 0 | 1 |
| 1 | X | 0 | 100XX | 00001 | 1 | 1 | 1 | 1 | 0 | 0 | 1 |
| X | 0 | 0 | X1X01 | 00001 | 1 | 1 | 1 | 1 | 0 | 0 | 1 |
| 0 | X | 0 | 0X00X | 00000 | 0 | 1 | 1 | 1 | 1 | 0 | 1 |

The X's in the above table indicate "don't care" condition.

An exemplary embodiment of logic circuit LGC1 will be described with reference to FIG. 19.

The external reset signal RESET, which is also supplied to LGC1, gives two internal reset signals: IRESN, obtained from signal RESET via logic inversion by inverter INV1; and RESER, obtained as logic OR of signals RESET and WRIN in circuit OR1.

Figure 18:
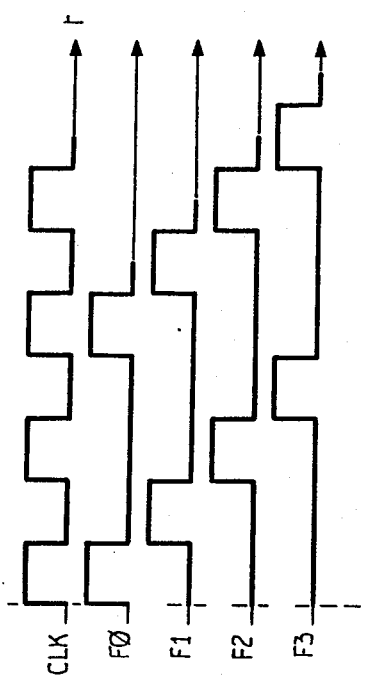
FIG. 18 shows a time graph of the four-phase internal clock signal.

CKDIV indicates a normal logic divider for extracting, from the external signal CLK, four internal synchronism phase signals F0, F1, F2, F3, having a frequency of 8 MHz, a 25% duty cycle, a quarter-period phase shift, as shown in FIG. 18, and supplied over bus FCLK.

CKDIV is reset by signal RESET, while phase signals F1 and F3 are ued for synchronizing LGC1 together with signal CLK.

Figure 11:
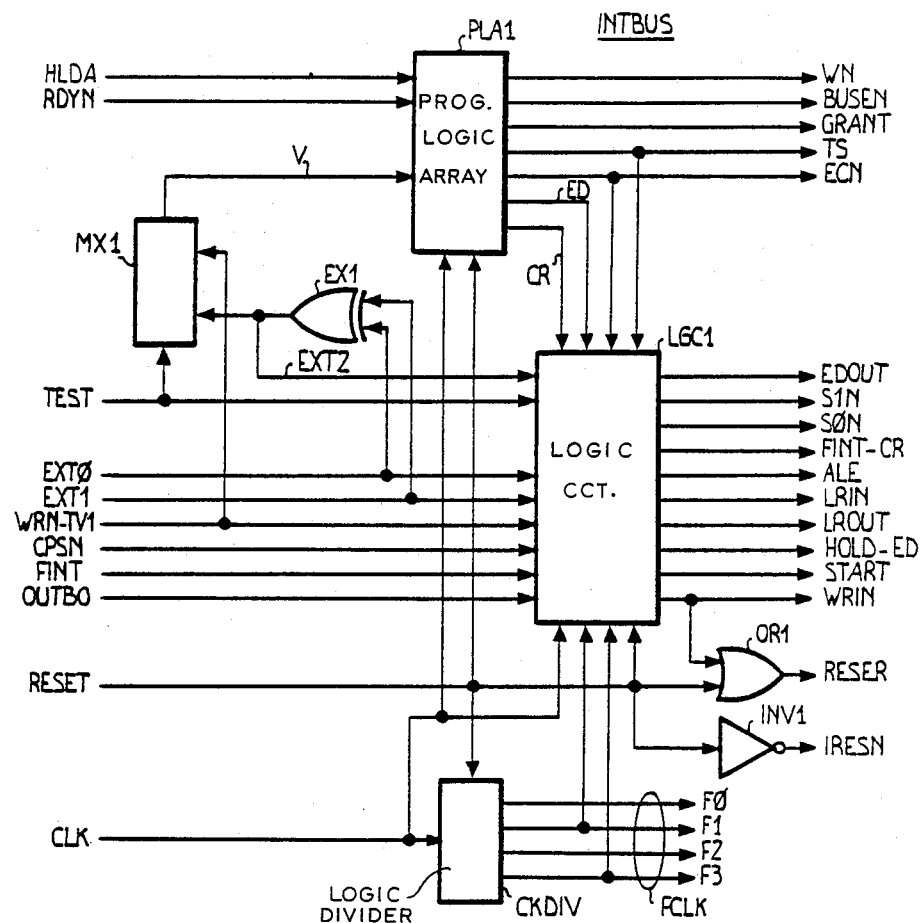
FIG. 11 shows a circuit diagram of block INTBUS in FIG. 10.
Figure 12:
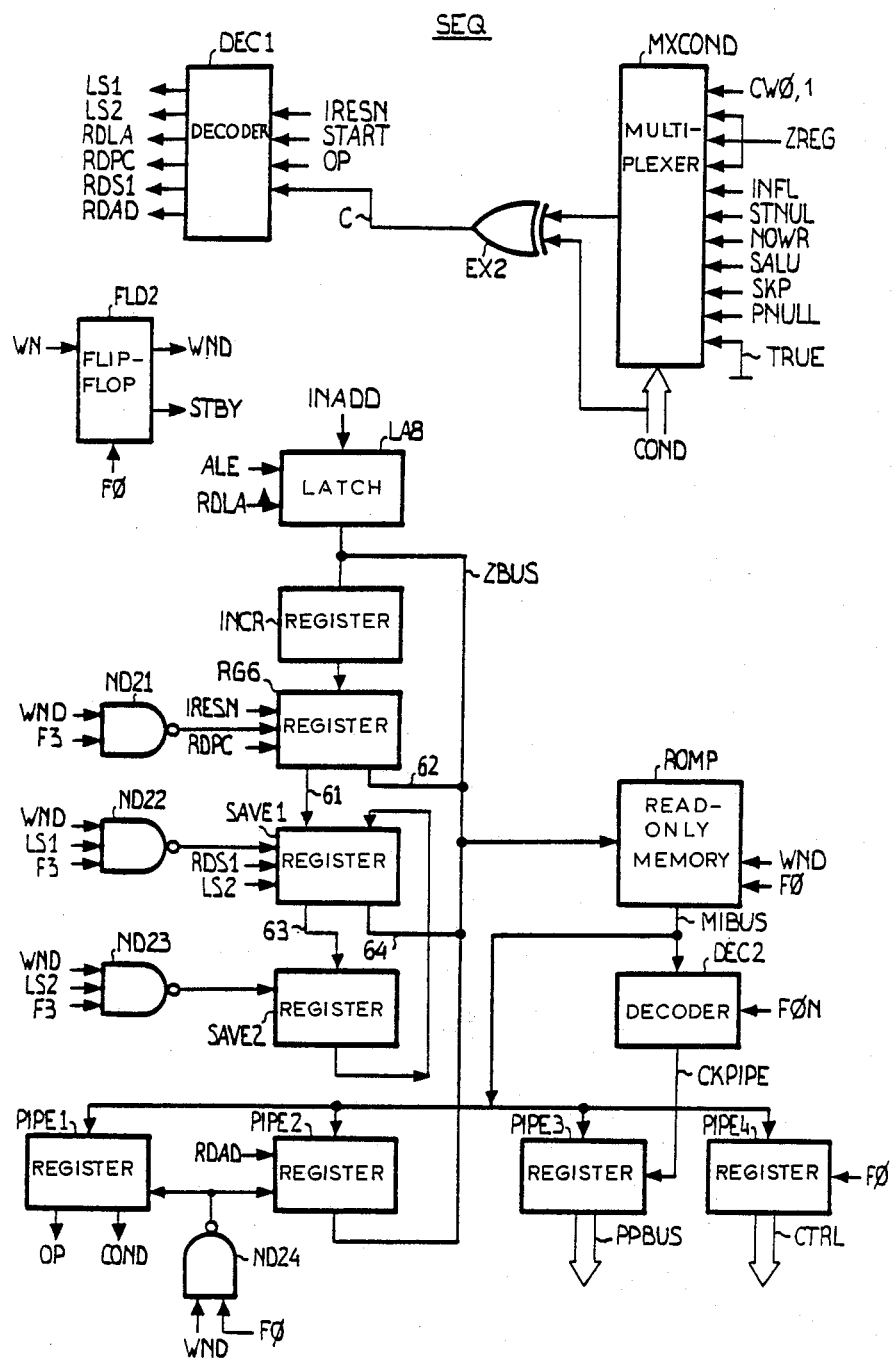
FIG. 12 shows a circuit diagram of block SEQ in FIG. 10.

Block LA8 in FIG. 12 provides for performing a known "latch" logic function. On receiving load command ALE from INTBUS block (FIG. 11), LA8 memorizes a starting address for the microprogram memory, which address is supplied from the outside via bus INADD, and is issued over tristate busABUS upon LA8 receiving a read control signal RDLA generated by block DEC2.

INCR indicates a normal incrementer for one-unit increment of the logic value on ZBUS and supply of the same to a normal resettable register RG6, which memorizes the output of INCR on receiving phase signal F3 supplied via NAND circuit ND21. The other input of ND21 is the wait signal WND generated by flip-flop FLD2 by synchronizing signal WN (from INTBUS, FIG. 11) with phase signal F0. In the presence of WND the content of RG6 relative to the foregoing microinstruction is frozen. In the presence of reset signal IRESN from INTBUS (FIG. 11), RG6 is reset.

In the presence of a read signal RDPC from block DEC1, the content of RG6 is supplied onto output buses 61 and 62.

Output 62 is a tristate bus connected to ZBUS, whereas output 61 is a normal bus connected to an input of block SAVE1.

Blocks INCR and RG6 act as a microprogram counter.

SAVE1 is a normal register which also provides for an additional input select function via the logic level of signal LS2 generated by block DEC1. The two selectable inputs are output 61 of RG6 and the output of a register SAVE2. The load signal for SAVE1 is the output of circuit ND22, which performs a logic NAND operation of signal LS1 generated by DEC1 and wait signal WND which may freeze the content of SAVE1. On receiving read signal RDS1 generated by DEC1, SAVE1 supplies its content onto output bus 64, said content still being retained, however, on output bus 63. Output 64 is a tristate bus connected to ZBUS, whereas output 63 is a normal bus connected to the input of register SAVE2.

The register SAVE2 memorizes output 63 of SAVE1 on receiving a load signal from the output of circuit ND23, which performs a logic NAND operation of phase signal F3, select signal LS2, employed here as a load signal, and wait signal WND which may freeze the content of SAVE2. The output of SAVE2 is always available at one of the inputs SAVE1.

Registers SAVE1 and SAVE2 provide for performing a known two-level-nesting stack function, for memorizes one or two re-entry addresses from a subroutine.

PIPE2 is a register forming part of the microinstruction storage register battery, and which memorises the next microinstruction address in the event of a branch or call to a subroutine. The said address, which is present on a number of wires of microinstruction bus MIBUS, is loaded into PIPE2 subsequent to enabling by the output signal of circuit ND24, which performs a logic NAND operation of phase signal F0 and wait signal WND which may temporarily freeze the content of PIPE2. The said content is supplied onto ZBUS in the presence of a read signal RDAD generated by DEC1. DEC1 is a normal decoder for producing read signals LS1, LS2, RDLA, RDPC, RDS1 and RDAD on the basis of the following input signals: start and reset signals START and IRESN from bus interface INTBUS (FIG. 11); operation code OP from register PIPE1; and condition bit C.

MXCOND is a normal multiplexer for performing a condition bit selection function. Depending on the bit combination on connection COND, MXCOND supplies one of the condition bits to EX-OR circuit EX2. A second input of EX2 is supplied with a further bit on connection COND, for supplying the true or complement value of the output bit of MXCOND on condition wire C.

The following condition bits are supplied to inputs of MXCOND:
CW0: bit in location 0 of control word CW Markov/-prototypical model coding.
CW1: bit in location 1 of control word CW.
ZREG: consists of three wires, each carrying the coding of a zero if any, in an internal register of block MREG (FIG. 13).
INFL: active when the first active state sa is detected in a node na.
STNUL: indicates an inactive state that has just been processed.
NOWR: disables writing of the dynamic programming result in area LAV and, like INFL and STNUL, is supplied over bus CTRL by block MEMI (FIG. 17).
SALU: sign bit from ALU (FIG. 16).
SKP: from block LSKIP (FIG. 17), the description of which explains the signal meaning.
PNULL: most significant bit of the word on BUSIN (e.g. for checking field A of some of the words in area PUSH).

TRUE: bit permanent at logic level 1 characterising an unconditional branch or call situation.

ROMP indicates a read-only memory containing the microinstructions addressed by the content of ZBUS and available on microinstruction bus MIBUS.

ROMP is composed of 256 43-bit words shared between operation and test microinstructions.

ROMP comprises a resettable output register, sending the microinstructions onto MIBUS in correspondence with phase signal F0. The output reset command consists of wait signal WND, in the presence of which no operations are performed.

An all-zero output code corresponds with a NOP (no operation) microinstruction.

PIPE1, PIPE2, PIPE3 and PIPE4 are registers or register batteries for temporarily storing, according to a known "pipeline" technique, the microinstruction fields on MIBUS. Provision has also been made for reducing the number of microinstruction bits, by enabling the same field in successive microinstructions to be stored in different registers in successive cycles, by each of which registers it is stored for a number of cycles, thus providing for an expansion of the microinstruction format.

PIPE1 contains two registers for storing microinstruction fields OP and COND when enabled by the output of gate ND24, i.e. at each pulse of phase signal F0, providing wait signal WND is not active.

The 2-bit field OP codes the following types of operation:
normal mode, with microprogram counter increment;
conditional branch;
conditional call to a subroutine;
condition return from a subroutine.

Field COND comprises four selection bits for multiplexer MXCOND, plus a bit for checking the true/complement condition.

PIPE2 comprises the aforementioned register containing the microinstruction address field.

PIPE3 comprises a battery of registers for storing microinstruction fields to be stored for a number of cycles and available on output bus PPBUS. The load control signals for each register in PIPE3 are supplied on connection CKPIPE by the output of decoder DEC2 which, depending on the bit combination of a field in each microinstruction received over a number of wires of MIBUS, accordingly inhibits a number of pulses in the complement phase signal FON for each of the said registers.

PIPE4 contains a register for storing, in the presence of phase signal F0, the microinstruction fields usually varying at each cycle, for supplying the same onto output bus CTRL.

FLD1 also generates signal STBY for disabling the read and write memories in RIPAC.

Figure 13:
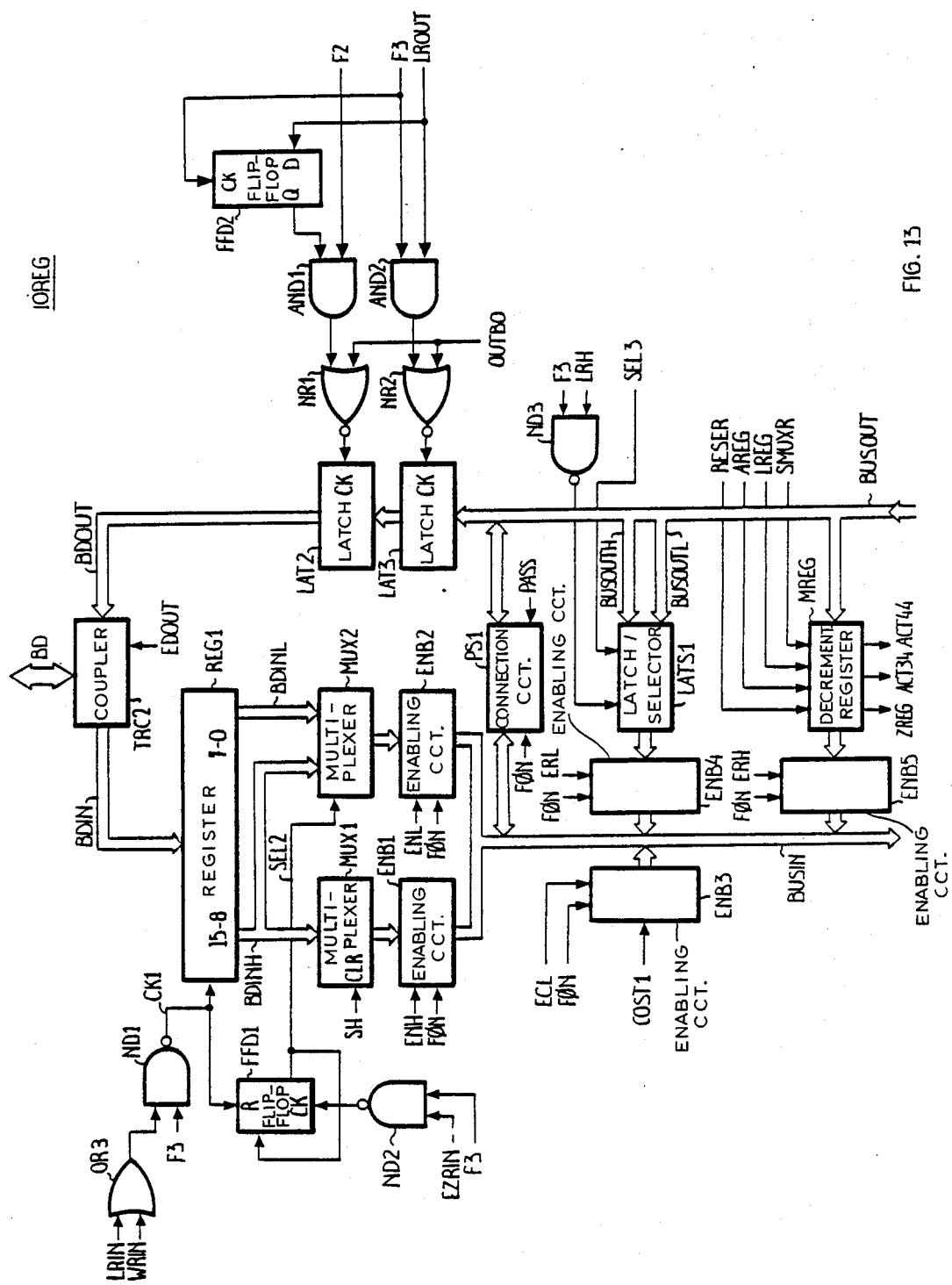
FIG. 13 shows a circuit diagram of block IOREG in FIG. 10.

TRC2 in FIG. 13 is a two-way coupler for connecting external two-way bus BD to data input bus BDIN or data output bus BDOUT, depending on the logic level of signal EDOUT supplied by INTBUS (FIG. 11). BDIN and BDOUT are 16-bit one-way buses.

REG1 is a register for suppling the 8 most significant and 8 least significant bits on bus BDIN to buses BDINH and BDINL respectively, depending on the logic level of the output signal from NAND circuit ND1. The inputs of ND1 consist of phase signal F3 and the output signal of logic circuit OR3, which performs an OR function of signals LRIN and WRIN coming from block INTBUS (FIG. 11) and controlling data input from the external bus.

MUX1 is a multiplexer which normally provides for reception and connection to the output of bus BDINH. On receiving control signal SH, however, it provides for forcing the outputs to logic level 0. The outputs of MUX1 are sent to a conventional enabling circuit ENB1 which, synchronized by the complement phase signal FON and enabled by signal ENH, supplies them on to the 8 most significant wires of BUSIN.

MUX2 is a two-input multiplexer for receiving buses BDINH and BDINL, which are connected to the output on the basis of selection signal SEL2. The latter is generated by the complement output of D type flip-flop FFD1 which receives signal CK1 at its reset input and, at its clock input, the output of circuit ND2 which performs a NAND function of control signal EZRIN and phase signal F3.

The outputs of MUX2 are sent to enabling circuit ENB2 which, synchronized by the complement phase signal FON and enabled by signal ENL, supplies them onto the 8 least significant wires of BUSIN.

If the EZRIN signal is not active MUX2 normally transfers the least significant bits on bus BDIN bus (bus BDINL onto the least significant wires of BUSIN. If EZRIN is active, however, MUX2 transfers first the least and then the most significant bits of BDIN onto the least significant wires of BUSIN in two successive stages. This dual switch of MUX2 is generated by flip-flop FFD1.

The following data transfers from BDIN to BUSIN are then performed via the logic already described:
normal transfer of the content of BDIN to BUSIN in the space of one microinstruction;
transfer of the least significant and then the most significant part of BDIN to the least significant part of BUSIN in two successive microinstruction cycles: in both phases, the most significant part of BUSIN is forced to logic level 0 by MUX1.

ENB3 is a further enabling circuit which, synchronized by the complement phase signal FON and enabled by signal ECL, provides for transferring a constant COST1 to the least significant part of BUSIN. In this case, the most significant part of BUSIN is forced to logic level 0 by MUX1.

LAT2 and LAT3 are two cascade-connected latches forming a register composed of master slave flip-flop elements. The clock signals for LAT2 and LAT3 are supplied respectively by NOR circuits NR1 and NR2, noth of which receive control signal OUTB0 (FIG. 11). NR2 also receives the signal generated by AND circuit AND2, which receives control signal LROUT and phase signal F3. NR1 also receives the signal generated by AND circuit AND1, which receives phase signal F2 and control signal LROUT delayed by one microinstruction cycle by D type flip-flop FFD2 synchronized by phase signal F3.

LAT3 and LAT2 provide for writing data from BUSOUT data onto BDOUT in the space of 2 microinstruction cycles, said write operation being controlled by signal LROUT from INTBUS (FIG. 11).

The external signal OUTB0, which also acts on signal EDOUT (FIG. 11), provides for direct external reading of the content of BUSOUT for test purposes.

PS1 is a connection circuit which, on receiving control signal PASS, provides for two-way data transfer between BUSIN and BUSOUT. PS1 consists of two enabling circuits synchronized by the complement phase signal FON.

Block LATS1 acts as both a latch and a selection circuit for selecting one of two inputs consisting of buses BUSOUTL and BUSOUTH carrying the 8 least and most significant bits of BUSOUT respectively.

Depending on the logic level of selection signal SEL3, and on receiving a control signal consisting of the output of NAND gate ND3, the inputs of which are supplied with signal LRH and phase signal F3, LATS1 connects one of the two input buses to enabling circuit ENB4, which transfers the output o LATS1 onto the most significant wires of BUSIN, when enabled by the ERL signal. ENB4 is synchronized by the complement phase signal FON.

Block MREG contains a decrementing register and three conventional registers, for performing the following functions: the logic level of control signal SMUXR determines either the decrementing or the loading of the content of BUSOUT by the decrementing register; the levels on connection AREG determine in which of the said three registers the content of the decrementing register is to be loaded and made available at the output; in the event of the said decrementing operation reaching 0, the register containing the said 0 is indicated on connection ZREG.

Figure 17:
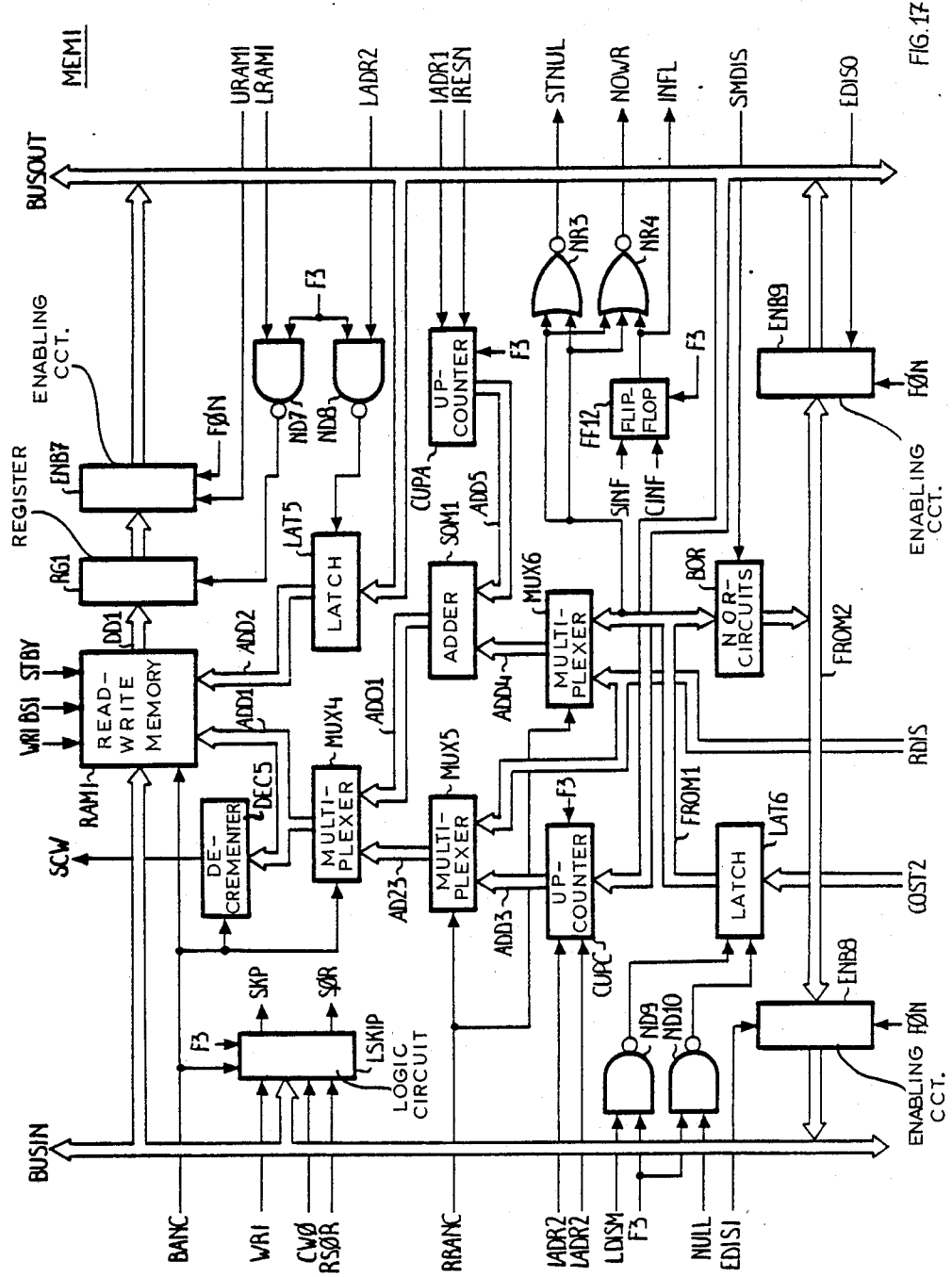
FIG. 17 shows a circuit diagram of block MEMI in FIG. 10.

One of the three registers is loaded with field SURV containing the number of active arcs na in the current frame, as defined in the foregoing description of dynamic programming operation OPD (ta) and present in bank B3 of the internal memory in MEMI (FIG. 17).

Via a control signal on wire LREG, the logic levels of the overflow bit and 2 most significant bits in the register are checked. If the overflow bit is present, an alarm signal ACT44 is generated to indicate attainment of the maximum processing capacity of the component. If, instead of the overflow bit, the two most significant bits present a logic level 1, an alarm signal ACT34 is generated to show that ¾ of maximum processing capacity has been exceeded.

Data output of MREG is supplied onto the least significant wires of BUSIN via enabling circuit ENB5, when the latter is enabled by signal ERH. ENB5 is synchronized by the complement phase signal FON. Registers MREG are reset by signal RESER signal from block INTBUS (FIG. 11).

Signals SH, ENH, ENL, EZRIN, ECL, PASS, LRH, SEL3, ERL, ERH, SMUXR, and LREG are supplied by bus CTRL, and value COST1 by bus PPBUS bus of sequencer SEQ (FIG. 12). ENC1 in FIG. 14 is an encoder for coding alarm signals ACT34 and ACT44 supplied by block IOREG (FIG. 13) over bus CTRL; WORK34 and WORK44 supplied by block ADR block (FIG. 14) over bus CTRL; and ECRC.

Each of the alarm signals is coded, by the same block generating it, with a bit pair in 1-out-of-2 code, which code considers bit pairs 10 and 01 valid and pairs 11 and 00 invalid. Said coding, which is performed for reliability purposes, provides for detecting additional failure caused by breakdowns on the respective lines. One valid bit pair indicates the absence and the other the presence of an alarm. An invalid pair indicates failure.

On output connection SW03, ENC1 produces a set of four bits in 2-out-of-4 code (two logic levels 1 out of four in the absence of failure) depending on the input bit configuration and according to the following coding system:

| SW03 | Type of alarm |
| --- | --- |
| 0011 | No alarm |
| 0101 | on input ECRC |
| 0110 | on input ACT34 |
| 1001 | on input WORK34 |
| 1010 | on input ACT44 |
| 1100 | on input WORK44 |

Any other bit configuration on SW03 indicates a code error caused by failure on the inputs or in the encoder itself.

In the event of simultaneously incoming alarm signals, the alarm codes in the above table are supplied by ENC1 to SW03 according to the following priority rating: alarm on ECRC (top priority condition), WORK44, ACT44, WORK34, ACT34, no alarm.

The bit configuration on SW03 is memorized in register SWRG in the presence of phase signal F3 supplied to the clock input of SWRG via NAND cicuit ND18, and is hereinafter referred to as state word SW.

In the presence of any alarm signal, ENC1 generates an interrupt signal INTI.

Signal INTI is memorized in flip-flop FFD3 which is synchronized by phase signal F3 via OR circuit OR4, the second input of which receives the output of FFD3, i.e. interrupt signal FINT which is later supplied to the block LGCIH (FIG. 9) via block INTBUS (FIG. 11).

Signal FINT thus remains active until the relative interrupt request is serviced by the master unit, subsequent to which reset signal RESER is sent to FFD3. Up to this point, further word storage in register SWRG is disabled so as to prevent overrunning, by supplying the complement of signal FINT to the second input of circuit ND18.

CWRG indicates a register for storing a 5-bit configuration, hereinafter referred to as control word CW, supplied at each frame by the master via the external memory area MAIL (FIG. 9) and copied by the slave into register CWRG at the initialization stage. The said control word is selected by an address bit configuration of bank B3 in RAMI(FIG. 17) and, when present in the least significant portion of BUSIN, is loaded into CWRG upon command of load signal SCW (from block MEMI in FIG. 17), synchronized by phase signal F3, supplied to the register via NAND circuit ND19. All the bits in the control word are available on connection CW04 forming part of bus CTRL.

The bits in control word CW indicate:

| Bit location | Logic level | Description |
| --- | --- | --- |
| 0 | 0 | Prototypical word β models |
|   | 1 | Markov word models |
| 1 | — | Available |
| 2 | 1 | Area VOC composed of Wi = 1024 × 4 contexts |
|   | 0 | Area VOC composed of Wi = 128 × 32 contexts |
| 3, 4 | 0 0 | Size of area LAV: 8K words |
|   | 0 1 | Size of area LAV: 16K words |
|   | 1 — | Size of area LAV: 32K words |

At the end of the frame, words SW and CW are supplied on to BUSOUT for copying into external memory area MAIL, and are transferred respectively into the most and least significant portions of BUSOUT, via enabling circuits ENB13 and ENB14 enabled by control signal EBUSOU in the presence of signal SCW synchronized by the complement phase signal FON via NAND circuit ND20.

CRC is a circuit for generating an alarm signal ECRC for encoder ENC1.

CRC is structured in substantially known manner, and consists of a sequential logic circuit which, at each microinstruction cycle, changes its internal state as a function of the logic configuration on bus BUSIN read in phase F3. CRC is used during testing for generating any known type of cyclic redundancy code of all the partial test result data on BUSIN relative to the partial result of the individual test phase. At the end of each test phase, CRC contains the cyclic redundancy code of the said test procedure, and BUSIN is supplied with a last word which, in the presence of control signal TST, is compared with the said code in CRC. Depending on the outcome of the said comparison, CRC generates a negative test ECRC alarm configuration or a positive test configuration of ECRC.

At the start of each test procedure, a signal RESER is supplied resetting the sequential circuits, in CRC.

Internal testing is performed by means of special subroutines occupying a specific part of the microprogram storage area. Each subroutine may be performed independently and called up from the outside by forcing onto buses BA and INADD the starting address in the microprogram memory in SEQ.

The said subroutines are either performed off line or during long silent or low system load periods, and are substantially as follows:

Testing of the memories MEMIN and MEMOF in block ADR, and memory bank B3 in RAMI in block MEMI. The said memories are loaded with test data using the same procedures as for initialization in the operation microprogram. The data on BUSIN in both this and the following test phases enables CRC to generate the said cyclic redundancy code, which is compared at the end of the test phase with a predetermined reference word supplied from the outside on BUSIN. This and all the other test phases are followed by a check phase wherein SEQ supplies a control signal TST for generating the state word SW to be supplied to the master and containing the test result in the form of the result of the said comparison. Following this test phase, the memories may be reloaded with work data which is left unerased in subsequent test phases.

Figure 15:
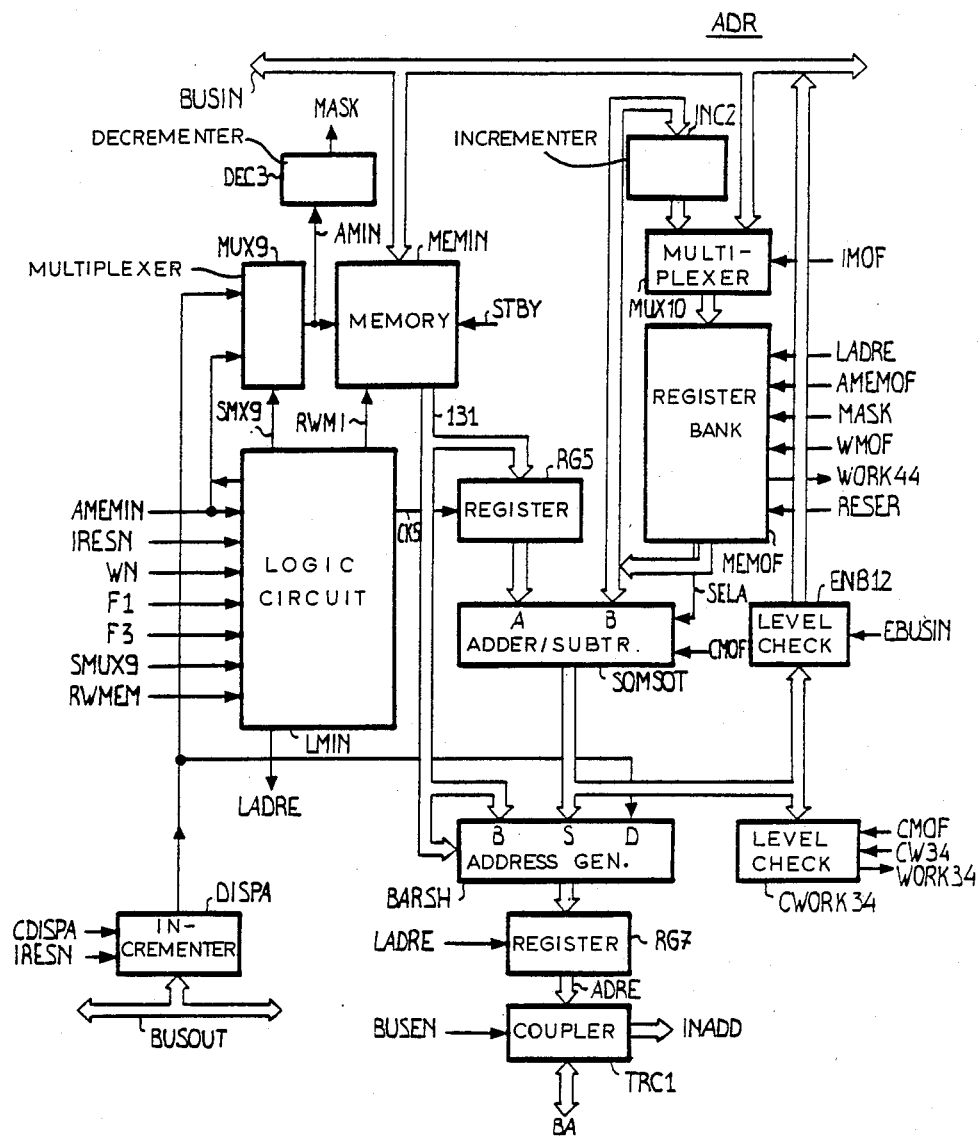
FIG. 15 shows a circuit diagram of block ADR in FIG. 10.

Testing of the block BARSH in ADR (FIG. 15). This test phase is performed separately from the previous one in that the master is also required to read the output data from this block, which is only available on bus BA. A check phase follows, as in the previous case.

Testing of banks B0, B1, B2 in memory RAMI (FIG. 17). A basic address in memory MEMIN is used for addressing a further external memory area containing the test data read from and written into the said banks. The entire block MEMI is then tested using the said data, after which, a check phase is performed.

Testing of unit ALV, using data loaded into bank B0, as in the previous case, the check phase follows.

Testing of INTBUS by means of a special, exclusively off-line procedure.

Testing of SEQ, by performing part of the operation microprogram on normally loaded test data sequences.

Signal SCW is supplied over PPBUS, and signals EBUSOU and TST over bus CTRL of SEQ (FIG. 12).

Memory MEMIN in FIG. 15 contains 32 16-bit words assigned in pairs to consecutive addresses: one out of the 16 even address words containing address $MEMIN_L(i)$ and one out of the 16 odd address words, containing the 7 address bits $MEMIN_H(i)$, plus a further 5 bits used for controlling block BARSH.

The addresses for MEMIN are supplied by the output signal from multiplexer MUX9. Write data is supplied over BUSIN, and read data over 16-bit bus 131.

MEMIN is a static read and write memory with static column precharge, and is disabled by signal STBY from SEQ (FIG. 12) when the component is disabled, so as to drastically reduce static power consumption.

DISPA is a normal resettable 8-bit incrementer, which is loaded with the content of BUSOUT. DISPA receives load or increment signals via the connection CDISPA, and is reset by signal IRESN from INTBUS (FIG. 11). The output of DISPA is supplied to an input of MUX9 for write-addressing memory MEMIN, and to an input of block BARSH input for preparing the external memory address. Only the 5 least significant bits of the DISPA output are supplied to MUX9.

Writing in MEMIN is performed normally during initialization. The incrementer DISPA provides for addressing all of the 16-bit words in MEMIN supplied in the writing phase via BUSIN. Storage of a word pair thus requires two write cycles.

LYMIN indicates a logic circuit controlling reading and writing in MEMIN

For writing in MEMIN, LMIN simply supplies MUX9 with signal SMX9 for selecting the input connected to DISPA, and MEMIN with signal RWMI.

For reading MEMIN, the input of MUX9 is switched to connection AMEMIN As both words in each pair have to be supplied on bus 131 in the space of one read cycle, the least significant bit of AMEMIN is supplied, not to MUX9, but to LMIN, which replaces it with a bit presenting logic level 0 in phase F1 and logic level 1 in phase F3. Thus, in a read cycle, whereas the four most significant bits of AMENIN address a word pair, in phase F1 field $MEMIN_L(i)$ of the first word is supplied on bus 131 and memorised in register RG7 appropriately clocked by the signal CK5 supplied by LMIN, and, in F3 phase, field $MEMIN_H(i)$ and the check bits of the second word are supplied directly on bus 131 to the BARSH block.

In test mode, MEMIN may be read- and write-addressed via both DISPA and field AMEMIN.

LMIN also generates a LADRE signal for loading register RG7.

The sequential circuits in LMIN are reset by signal IRESN, but data may be temporarily frozen in them by signal WN. Both IRESN and WN are supplied by block INTBUS (FIG. 11).

MEMOF functionally comprises a bank of four registers accessed individually, by means of selection signals AMEMOF, jointly with control signal WMOF for write access, and the signal LADRE generated by LMIN for read access.

The data input for registers in MEMOF is the output of multiplexer MUX10, the two inputs of which are selected by signal IMOF and connected to BUSIN and the output of a normal incrementer INC2, the input of which is the data output of MEMOF.

The registers in MEMOF may thus be loaded with fixed bit configurations supplied by BUSIN and possibly incremented by INC2.

In the event of cyclical addressing by ADR, the outputs of MEMOF may be partially or totally masked via a control signal on connection MASK on which presents a decoding, made by decoder DEC4, of the most significant bits of the output AMIN of MUX9.

This operation is required by virtue of the size of a number of external memory areas (such as area LAV in FIG. 4) being varied from the outside by the bits in the second to fourth location in control word CW (FIG. 11) which are also present on connection MASK. A change in the size of the said external memory areas also involves changing the counting module for the cyclical addressing generated via incrementer INC2, for preventing unpermitted areas from being addressed. Masking consists in keeping the most significant output bits of MEMOF at logic level 0.

Total masking of output MEMOF is provided for by signal SELA generated in MEMOF and which disanles input B of adder SOMSOT.

MEMOF also contains a comparison circuit for generating alarm signal WORK44 supplied to DIAG (FIG. 14) and indicating that maximum capacity of area LAV (FIG. 3) has been reached, and any further writing in LAV will erase words still of use. The said comparison circuit checks matching of read and write pointing addresses at area LAV present at all times in two registers of MEMOF and incremented at each read and write operation in LAV respectively.

The internal MEMOF registers are reset by signal RESER (FIG. 11).

The outputs of register RG5 and MEMOF are supplied, as operands A and B respectively, to a normal 16-bit adder/subtracter SOMSOT for performing an A+B or A−B operation depending on the logic level of control signal CMOF.

In the presence of signal SELA, instead of performing an addition, SOMSOT supplies the value of input A directly.

In normal address mode, SOMSOT performs addition $MEMIN_L(i)+MEMOF(j)$ in the formula of address ADRE.

At the end of each frame, SOMSOT may also perform subtraction TOP−FREE wherein TOP is contained in one of the words from MEMIN and FREE is supplied by one of the registers in MEMOF. In this case, the two most significant bits in the result at the output of SOMSOT are supplied to block CWORK34 block which, enabled by signal CMOF indicating subtraction, checks the logic level of the said two bits. If both are 0, this means area LAV has been filled to at least ¾ of maximum capacity, in which case, an alarm signal WORK34 is generated and supplied to block DIAG (FIG. 14).

As the size of area LAV is variable and determined by the bits in the third and fourth location in control word CW, it follows that the locations of the two most significant bits in the result of the subtraction made in SOMSOT may also vary: the combination of the said bits of CW suplied to CWORK34 via the connection CW34 selects the two wires in the output bus of SOMSOT on which to perform the check.

The result of the operation performed by SOMSOT may also be supplied onto BUSIN via enabling circuit ENB12, when this is enabled by signal EBUSIN.

BARSH indicates a circuit known as a "barrel shifter" consisting of a battery of multiplexers for shifting inputs by a variable number of positions within a brief, fixed time period. This is used in place of usual shift registers for increasing shift speed.

The function of circuit BARSH is to provide address ADRE according to the aforementioned formula. Input B is supplied with the term $MEMIN_H(i)$, input S with sum $MEMIN_L(i)+MEMOF(j)$, and input D with the term DISPA from incrementer DISPA.

BARSH shifts the bits on inputs B and S by W positions, W being equal to the number of bits in field DISPA. The coding of number W is supplied to the control input of BARSH by the most significant bits on bus 131 containing the second of the two words read in MEMIN.

Number W is variable by virtue of the number of words in the record being addressed varying as a function of the individual external memory table. In the example shown, W=0, 1, 2, 7, 8.

The following ADRE value will be present at the BARSH output:

$$ADRE = 2^{16+W} \cdot B + 2^W \cdot S + D_{module\ 223}$$

As the addresses generated are of constant 23-bit size, W most significant bits in BARSH will obviously be lost and replaced by W least significant bits of the output of DISPA.

On the basis of the formula giving address ADRE, a technician skilled in the art is capable of designing block BARSH.

Access is thus afforded to each individual table in the external memory via the content of MEMIN, to a specific block in the table via the content of MEMOF, and to a specific word in the block via incremente DISPA.

The output of BARSH is supplied to register RG7, which temporarily stores address ADRE and supplies it on to output bus ADRE when synchronized by signal LADRE generated by circuit LMIN.

TRC1 is a normal coupler for two-way connection of one-way buses ADRE and INADD to two-way external bus BA. Controlled by the signal BUSEN generated by INTBUS (FIG. 11), TRC1 transfers the content of bus ADRE onto bus BA, or the conent of the 8 least significant locations of BA onto INADD bearing an external starting address for the microprogram memory ROM of sequencer SEQ (FIG. 12).

The signals on connections AMEMIN and AMEMOF are supplied over PPBUS (FIG. 11), and signals SMUX9, RWMEN, CDISPA, CMOF, IMOF, WMOF, EBUSIN and MASK over bus CTRL (FIG. 11).

Figure 16:
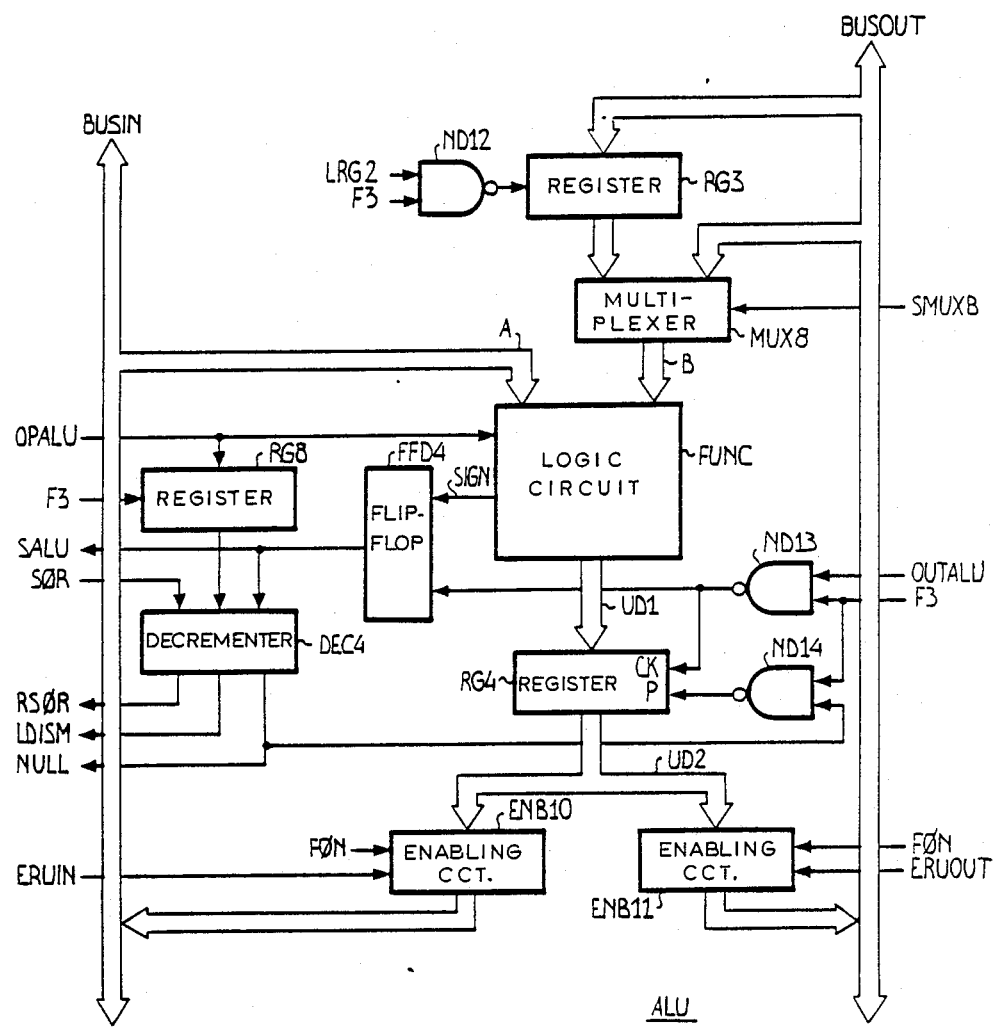
FIG. 16 shows a circuit diagram of block ALU in FIG. 10.

RG3 in FIG. 16 is a register for temporarily storing the content of the 12 least significant wires of BUSOUT or reception of control signal LRG2 synchronized by phase signal F3 via NAND circuit ND12, and supplying the same to an input of multiplexer MUX8.

The other input of MUX8 is connected directly to the 12 least significant wires BUSOUT. MUX8 issues one of the said two inputs as a function of selection signal SMUXB.

FUNC is a combinatorial logic circuit constituting the processing unit of block ALU, with 12-bit data inputs and a 12-bit data output. FUNC receives the 12 least significant BUSIN bits as operand A, and the MUX8 output as operand B.

The code indicating the type of operation to be performed is supplied on connection OPALU, and the overflow signal on wire SIGN. The data output bus UD1 of FUNC is sent to register RG4 which, on receiving control signal OUTALU synchronized by phase signal F3 via NAND circuit ND13, memorizes the content of UD1 and supplies it on to output bus UD2 as an operation result.

The following table shows the operations performed by FUNC together with the operation code (OPALU) and result on output bjus UD1.

| OPALU | OPERATION OF FUNC | Ud1 |
| --- | --- | --- |
| 0 0 | A + B | A + B |
| 0 1 | A − B | A + B |
| 1 0 | Comparison of item A with threshold B | All "1" (if A ≧ B) A (if A < B) |
| 1 1 | Minimum of A and B | A (if A < B) B (if A ≧ B) |

A and B in the above table indicate the operands at the inputs of FUNC.

If the result of A+B causes an overflow, all the FUNC outputs of UD1 will be at logic level 1 (saturated sum).

The following table shows the overflow signal level on wire SIGN depending on the type of operation and result.

| OPERATION | SIGN |
| --- | --- |
| A + B | 0 (no overflow) 1 (overflow) |
| A − B | 1 if A ≧ B 0 if A < B |
| Comparison of A and B | 1 if A ≧ B 0 if A < B |
| Minimum of A and B | 1 if A ≧ B 0 if A < B |

The foregoing operating description is sufficient to enable a technician skilled in the art to design the relative circuit FUNC.

The data on output bus UD2 may be supplied to BUSIN or BUSOUT via two respective enabling circuits ENB10 and ENB11 synchronized by the complement phase signal FON when these circuits are enabled by signals ERUIN and ERUOUT.

The operation code on the connection OPALU is temporarily stored in register RG8, which provides for supplying it and at the same time generating the signal SALU. The latter represents the overflow bit SIGN synchronized by D type flip-flop FFD4, the clock input of which is connected to the output of circuit ND13. SALU is also supplied as a condition signal to sequencer SEQ (FIG. 12).

DEC4 is a combinatorial circuit which receives signals SOR (from the block MEMI in FIG. 17), OPALU and SALU, and generates control signals RSOR, LDISM and NULL for the block MEMI according to the following truth table:

| OPALU | SALU | SOR | NULL | LDISM | RSOR |
| --- | --- | --- | --- | --- | --- |
| 0 X | X | X | 0 | 0 | 0 |
| 1 0 | 0 | X | 1 | 0 | 0 |
| 1 0 | 1 | X | 0 | 0 | 0 |
| 1 1 | 0 | 0 | 0 | 0 | 1 |
| 1 1 | 1 | 0 | 0 | 1 | 1 |
| 1 1 | X | 1 | 1 | 0 | 1 |

The X in the above table indicates a don't care condition.

Signal NULL is also supplied to the preset input of register RG4, synchronized by phase signal F3 via NAND circuit ND14, for forcing all logic 1's at the output.

Signals LRG2, SMUXB, OPALU, OUTALU, ERUIN and ERUOUT are supplied by SEQ (FIG. 12) over bus CTRL.

RAMI in FIG. 17 is a 64×16-word static-precharge read and write memory organized in four banks B0, B1, B2 and B3, in one of which reading and writing of individual bits is possible.

RAMI also receives the signal STBY from SEQ (FIG. 12) which may disable precharge as in the case of MEMIN (FIG. 15).

RAMI receives read/write control signal WRI, and signal BSI for selecting bit addressing of bank B2.

Write data to RAMI is supplied over BUSIN. Data read from RAMI is supplied over bus DD1 to BUSOUT via register RG1 and enabling circuit ENB7 in the microinstruction cycle following the read cycle. RG1 is synchronized by the output signal of NAND circuit ND7, the inputs of which are phase signal F3 and control signal LRAMI, whereas ENB7 is synchronized by the complement FON phase signal FON and enabled by control signal URAMI.

The signals selecting the bank to be addressed in RAMI are supplied on connection BANC, the bank word addresses on 4-wire bus ADDI, and the addresses of the single bit in the word of bank B2 on 4-wire bus ADD2.

The addresses of the single bit in the word of bank B2 are read from the four least significant locations in BUSOUT and supplied to the bus ADD2 via latch LAT5 synchronized by the output signal of NAND circuit ND8, the inputs of which are phase signal F3 and control signal LADR2.

MUX4 is a two-input multiplexer switchable onto output bus ADD1 by the signal on one of the wires of bank selecting connection BANC.

MUX4 is switched onto input bus AD01 for banks B0 and B1, and AD23 for banks B2 and B3.

MUX5 is a two-input multiplexer switchable onto output bus AD23 by selection signal RBANC. ADD3 and RDIS are the 4-wire input buses of MUX5.

SOM1 is a normal adder for supplying on to bus AD01 the added contents of 4-wire buses ADD4 and ADD5.

CUPC is a normal module-16 up-counter register into which is loaded the content of locations 7 to 4 off BUSOUT. The load and increment signals for CUPC are supplied over wires IADR2 and LADR2 respectively. CUPC is synchronized by phase signal F3, and supplies the count onto bus ADD3.

MUX6 is a two-input multiplexer switchable onto output bus ADD4 by the same selection signal RBANC as MUX5. MUX6 presents two 4-wire input buses RDIS and FROM1.

CUPA is a normal resettable module-16 up-counter register, the increment and reset signals of which are supplied over wires IADR1 and IRESN respectively. CUPA is synchronized by phase signal F3, and supplies the count onto bus ADD5.

LAT6 is a latch which, when enabled by signal LDISM, supplies the content of bus COST2, with the sign inverted, onto bus FROM1, and, on receiving control signal NULL, sets the outputs to logic level 0. Both signals LDISM and NULL signals are supplied to LAT6 by block ALU (FIG. 16) via two NAND circuits ND9 and ND10, the second inputs of which are supplied with phase signal, F3.

BOR is a block containing four NOR circuits, one for each wire of input bus FROM1, and the second input of which is supplied with a SMDIS signal. When the latter is 1, the NOR circuit outputs on FROM2 are 0, and when it is 0, FROM2 presents the complement of the content of FROM1.

The content of FROM2 may be supplied onto BUSIN or BUSOUT via enabling circuits ENB8 and ENB9 respectively, when the latter are enabled by signals EDISI and EDISO. ENB8 and ENB9 are synchronized by the complement phase signal, FON.

The following address modes are possible depending on which memory bank is selected:

Banks B0, B1: addressing of successive word groups via the sum, computed in SOM1, of the content of bus ADD5 (containing successive counts of CUPA) and RDIS, or of bus ADD5 and FROM1. This provides for local shifting (with 0, −1, −2 relocation) required for obtaining all the local dynamic programming operands. RDIS is a stored microprogram field used during the best path search for obtaining the best value of DG (bank B0). Value FROM1, on the other hand, may or may not be updated in LAT6 at each step in the best path search, depending on the result from block ALU (FIG. 16), and represents a stored relocation permitting reading of the location of field BCK (bank B1) corresponding to the best value of DG. FROM1 presents the complement of the relocation logic value, so that SOM1 calculates the sum of a negative relocation.

Bank B3: immediate word selection via the content of bus RDIS; selection of consecutive word groups via the output of counter CUPC. When the write-selected word is control word CW, the address on bus ADD1 and the code of bank B3 on BANC generate signal SCW in decoder DEC5 for block DIAG (FIG. 14).

Bank B2: as for bank B3, with the additional possibility of single-bit addressing via the content of bus ADD2. Both latch LAT5 and count register CUPC are loaded upon command of the same signal (LADR2) and contain field BCK of the 8 least significant bits of BUS-OUT, the four most significant of which are sent onto bus ADD3 for indicating the word, and the four least significant onto bus ADD2 for indicating the bit within that particular word. Block MEMI block also comprises a logic circuit for generating condition signals INFL, STNUL and NOWR for sequencer SEQ (FIG. 12).

When commencing processing of a new active arc na, an inactive state code is generated and, at the same time, SEQ (FIG. 12) emits signal CINF onto bus CTRL, which signal is sent to the reset input of flip-flop FF12, synchronized by phase signal F3.

When the first active state sa is idenfied, the sequencer generates signal SINF for the set input of FF12, which activates output signal INFL to show arc na is still active.

The two least significant bits of FROM1 are supplied to NOR circuits NR3 and NR4. When the said bits indicate an inactive state (negative logic code "00"), circuit NR3 generates signal STNUL to show an inactive state has just been detected, whereas circuit NR4, if signal INFL its third input is inactive, generates signal NOWR for preventing inactive states with an index below INF (the first active state) from being written into area LAV.

LSKIP is a logic circuit for performing the following functions:

when performing a write operation in bank B0 (as shown by a write signal WRI and the code of bank B0 on connection BANC), the inactive state code (logic levels "11") shown by the bits of field FROM on BUSIN is memorised in a three-position shift register synchronized by phase signal F3. A sequence of three consecutive inactive states generates a condition signal SK for the microprogram sequencer, for forcing an inactive state as the result of operation OPD (ta, na, sa) without terminating the same.

When performing a write operation in bank B0 using prototypical models, as shown by bit CWO in control word CW, a "00" code in the bits of field FROM bits on BUSIN indicating provenience from to the same state in the local best path search process, causes generation of signal SOR signal which, supplied to decoder DEC4 in block ALU (FIG. 16), disables load signal LDISM and generates signal NUL for loading an inactive state condition on FROM1 and so preventing the same state from being repeated more than once on a given search path. At the next phase signal pulse of F3, signal SOR is disabled by reset signal RSOR from block ALU (FIG. 16).

Signals COST2, RDI2, BANC and RBNAC signals are supplied via PPBUS, and signals WRI, BSI, IADR2, LADR2, EDISI, ESIDO, SMDIS, IADR1, LRAMI and URAMI via bus CTRL from sequencer SEQ (FIG. 12).

Figure 19:
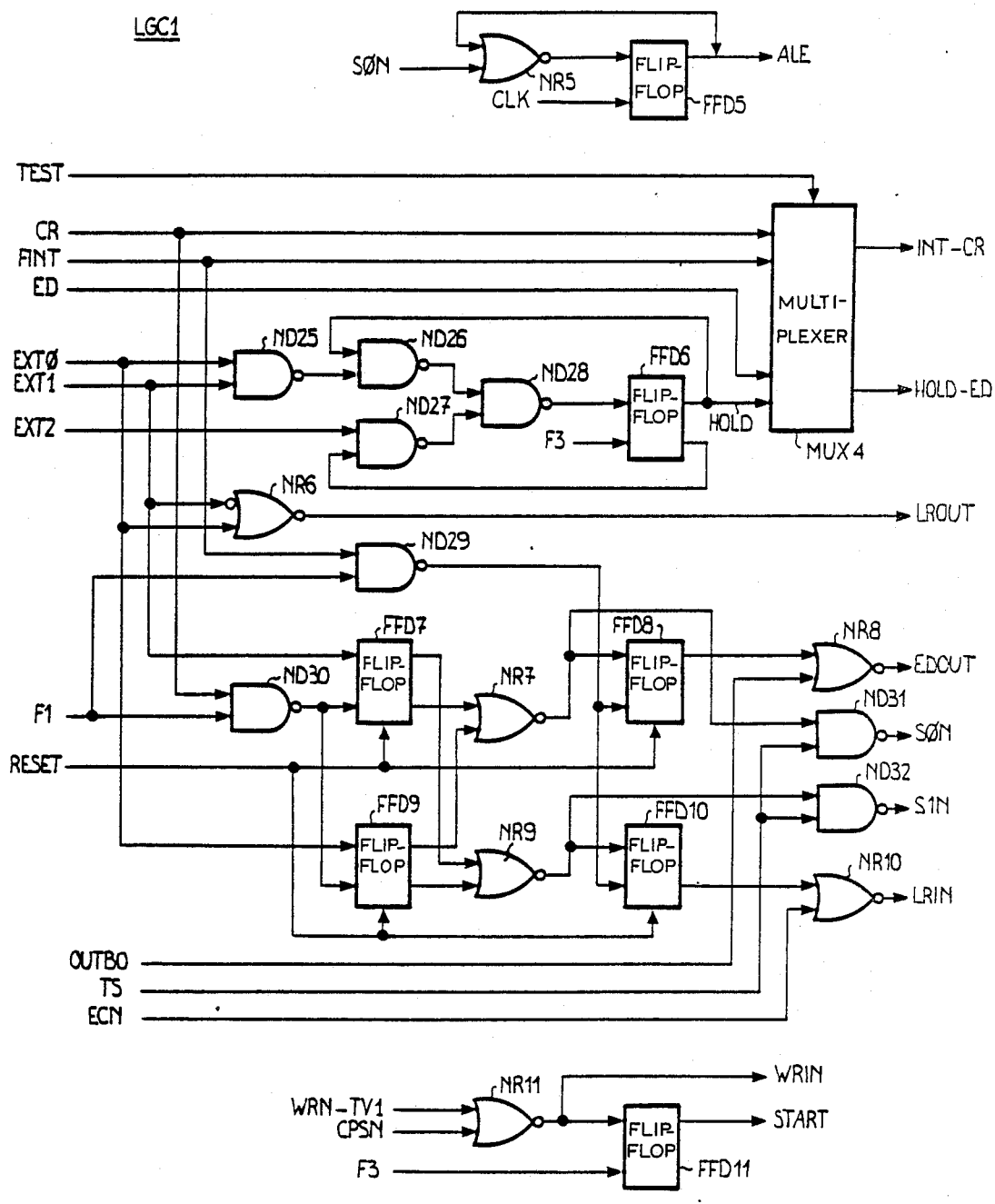
FIG. 19 shows a circuit diagram of block LGCI in FIG. 11.

In FIG. 19, FFD5, FFD11 indicate seven D type flip-flops; MUX4 a four-input, two-output multiplexer; NR5, ..., NR11 seven NOR gates; and ND25, ... ND32 eight NAND gates.

The "true" output of FFD5 is signal ALE produced by supplying the input with the output of NR5, the inputs of which are the said signals ALE and SON. The clock input of FFD5 is supplied with the signal CLK.

Controlled by signal TEST, MUX4 supplies outputs INT-CR and HOLD-ED respectively with signals FINT and HOLD in normal mode, and signals CR and ED in test mode. Signal HOLD is supplied by the "true" output of FFD6, which is also supplied to an input of ND26, whereas the complement output of FFD6 is supplied to an input of ND27. The outputs of ND26 and ND27 are supplied to ND28, the output of which is supplied to the input of FFD6 and the clock signal of which is F3.

The second input of ND27 is supplied with signal EXT2, and the second input of ND26 with the output of ND25, the inputs of which are signals EXT0 and EXT1.

The complements of signals EXT1 and EXT0 are supplid to NR6 which supplies an output signal LROUT.

The respective data inputs of FFD7 and FFD9 are EXT1 and EXT0, whereas the clock signal is the output of ND30, the inputs of which are signals F1 and CR. The true output of FFD7 and the complement output of FFD9 are supplied to NR9, the output of which is supplied to the input of FFD10 and an input of ND32.

The complement output of FFD7 and the true output of FFD9 are supplied to NR7, the output of which is supplied to the input of FFD8 and an input of ND31.

The clock input of FFD8 and FFD10 is the output of ND29, the inputs of which are signals F1 and ED.

The straight output of FFD8 is supplied to an input of NR8, the second input of which is supplied with an OUTBO signal for generating output signal EDOUT. The complement output of FFD10 is supplied to an input of NR10, the second input of which is supplied with signal ECN for generating signal LRIN. The second input of ND31 and ND32 is supplied with signal TS for respectively generating signals S0N and S1N. The RESET signal is supplied to the reset input of FFD7, FFD8, FFD9 and FFD10.

Signals WRN-TV1 and CPSN are supplied to the input of NR11, which supplies a output signal WRIN also supplied to the input of FFD11, the straight output of which is signal START. The clock signal for FFD11 is F3.

We claim:

1. A microprogrammed processing unit constituting the lower level of a two-level processing system, and comprising an interface circuit (INTBUS) for controlling two-way dialogue between the said unit and the higher level via two-way external control buses (BC), data buses (BD) and address buses (BA) also connected to an external data memory (MEME) accessed by both the said unit and the said higher level, and comprising a microinstruction sequencing unit (SEQ) supplying the microinstructions onto internal buses (CTRL, PPBUS), said microprogrammed processing unit comprising:

a connection circuit (IOREG) for transferring data from the said external data bus (BD) onto a first internal bus (BUSIN), or from a second internal bus (BUSOUT) onto the said external data bus, said first and second external buses being of the precharge type;

an arithmetical-logic unit (ALU) for receiving a first operand on the said first internal bus (BUSIN) and a second operand on the said second internal bus (BUSOUT), adding, subtracting, comparing or determining the minimum of the said first and second operands, and supplying the result on the said first or second internal bus;

a first read and write internal data memory (RAMI) organized in four banks (B0, B1, B2, B3) and which is loaded with the data on the said first internal bus (BUSIN) and supplies data onto the said second internal bus (BUSOUT);

a circuit (MEMI) for addressing the said first internal memory, which circuit provides for cyclically addressing words in the said first and second banks (B0, B1), addressing each bit in the said third bank (B2), and addressing words in the said fourth bank (B3);

a unit (ADR) for addressing the said external data memory (MEME) which is organized in tables consisting each of a specific number of word blocks; the said unit calculating a generic word address according to the sum of three terms: the location address of the first word in the table and present in a second internal memory (MEMIN); the address of the start block location in the table and present in a third internal memory (MEMOF); and the word location within the block; said addresses being supplied on the external address bus (BA).

2. The processing unit defined in claim 1 wherein the said unit (ADR) for addressing the said external data memory (MEME) calculates the said address according to the following equation:

$$ADRE = 2^{y+w} \cdot MEMIN_H(i) + 2^w \cdot [MEMIN_L(i) + MEMOF(j)] + DISPA$$

wherein: i and j are the indices of the single addresses present in the said second (MEMIN) and said third (MEMOF) internal memory respectively; $MEMIN_H$ and $MEMIN_L$ indicate the most and lest significant bits of the address in the said second internal memory; W is the number of bits, depending on each individual table, occupying term DISPA indicating a word within the block; and y is the number of bits in terms $MEMIN_L(i)$ and $MEMOF(j)$.

3. The processing unit defined in claim 1, wherein said sequencing unit (SEQ) employs a tristate internal bus (ZBUS) for supplying addresses to an internal microprogram memory (ROMP) containing microinstructions relative to an application microprogram and a test microprogram; and in that the said internal bus may be written on by a first latch circuit (LA8) carrying a starting address supplied from the outside over the said external address bus (BA) for enabling the said test microprogram; by a microinstruction incrementer (INCR, RG6); by a pair of registers (SAVE1, SAVE2) for memorising one or two subroutine reentry point addresses calculated by the said incrementer; and by a first register (PIPE2) for memorising a microinstruction address field; the said circuits permitted to write on the said internal bus (ZBUS) being selected by a decoder (DEC1) jointly controlled by the said interface circuit (INTBUS), a microinstruction operation code field (OP) and a condition bit (C) generated by an EX-OR circuit (EX2) which selects the true or complement condition of the output of a condition multiplexer (MXCOND).

4. The processing unit defined in claim 1, wherein said connection circuit (IOREG) comprises:

a first two-way coupler (TRC2) and enabling circuits (REG1, LAT2, LAT3) which, controlled by the said interface circuit (INTBUS), provide for transferring data between the said external data bus (BD) and the said first and second internal bus (BUSIN, BUSOUT);

a first multiplexer (MUX1) which, upon command by the said sequencer (SEQ), transfers the most significant locations of the said external data bus (BD) or logic 0's into the most significant locations of the said first internal bus (BUSIN);

a second multiplexer (MUX2) which, upon command by the said sequencer (SEQ), connects the most or least significant locations of the said external data bus to the least significant locations of the said first internal bus;

a mutual enabling circuit (PS1) which, when so controlled by the said sequencer (SEQ), provides for data exchange between the said first and said second internal bus;

a second latch circuit (LATS1) with an additional input selection function, and which, upon command by the said sequencer (SEQ), transfers the most or least significant locations of the said second internal bus (BUSOUT) into the most significant locations of the said first internal bus (BUSIN);

a register block (MREG) comprising a decrementing register into which is loaded the content of the said second internal bus (BUSOUT), and three registers selectable by the said sequencer (SEQ) and which, in addition to memorising and emiting the content of the said decrementing register on to the said first internal bus (BUSIN), also supply the said condition multiplexer (MXCOND) in the sequencer with a signal (ZREG) when their content is logic level 0.

5. The processing unit defined in claim 1, wherein said circuit (MEMI) for addressing the said first internal data memory (RAMI) substantially comprises:
- a third multiplexer (MUX4) controlled by a bank selecting signal (BANC) generated by the said sequencing unit (SEQ) and which supplies the said first data memory (RAMI) with addresses for the words in the said first or second bank (B0, B1) and present at a first input (AD01), or for the words in the said third or fourth bank (B2, B3) and present at a second input (AD23);
- a first adder (SOM1) for adding the output of a first resettable up counter (CUPA) enabled by the said sequencing unit (SEQ), and the output of a fourth multiplexer (MUX6) whose two inputs, selectable by the said sequencing unit, are a first microinstruction field (RDIS) supplied directly by the said sequencing unit, or a second microinstruction field (COST2) stored previously in a third latch circuit (LAT6); the said first adder (SOM1) supplying the results to a first input of the said third multiplexer (MUX4);
- a fifth multiplexer (MUX5) which, controlled by the said sequencing unit, supplies a second input of the said third multiplexer (MUX4) with the said first microinstruction field (RDIS) or the output of an up counter (CUPC) controlled by the said sequencing unit and programmable with the content of the most significant locations of the said second internal bus (BUSOUT);
- a fourth latch circuit (LAT5) which, upon command by the said sequencing unit, supplies the said third bank (B2) with the content of the least significant locations of the said second internal bus (BUSOUT) as a single word bit address.

6. The processing unit defined in claim 1, wherein said unit (ADR) for addressing the said external data memory (MEME) substantially comprises:
- the said second internal memory (MEMIN) organized in word pairs, the first word of which contains the said addresses $MEMIN_L(i)$, and the second word of which contains the said addresses $MEMIN_H(i)$ in the least significant locations, and the coding of the said bit number w in the most significant locations;
- a sixth multiplexer (MUX9) for supplying addresses to the said second internal memory (MEMIN);
- a second resettable up counter (DISPA) which may be loaded with the content of the said second internal bus (BUSOUT) upon command by the said sequencing unit (SEQ), the said counter supplying the count values to a first input of the said sixth multiplexer (MUX9);
- a first logic circuit (LMIN) for controlling addressing of the said second internal memory, which circuit receives from the said sequencing unit (SEQ), selection signals for word pair reading also supplied to a second input of the said sixth multiplexer (MUX9), and selects, for writing, the said first input of the said sixth multiplexer (MUX9), the said second internal memory being loaded, during initialization of the processing unit, with words supplied on the said first bus (BUSIN), and, for reading, the second input of the said sixth multiplexer (MUX9) by adding, in the least significant location of the said second input, a bit which changes logic level in the space of one internal clock signal period, so that, in a first phase of the said period, the first word in the said pair is read and memorised in a first register (RG5), and, in a second phase of the said period, the said first and second word in the said pair are simultaneously present at the output of the said first register and the output of the said second memory respectively;
- the said third internal memory (MEMOF) organized in registers addressable individually via control signals from the said sequencing unit; each said register temporarily storing one of the said addresses MEMOF(j) and being loaded directly with the content of the said first internal bus, possibly incremented by an incrementer (INC2) loaded by the output of the said third internal memory; the input for each said register being supplied by a seventh multiplexer (MUX10) which selects the said first internal bus or the output of the said incrementer;
- an adder-subtractor (SOMSOT) which, for addressing, normally adds the outputs of the said first register (RG5) and the selected register in the said third internal memory (MEMOF);
- a circuit (BARSH) for high-speed input shift which receives, at its data inputs, the outputs of the said second up counter (DISPA) and the said adder-subtractor (SOMSOT) and the least significant locations of the second word supplied by the said second internal memory (MEMIN), and, at its control input, the coding of the said number w in the most significant locations of the said second word; which circuit (BARSH) compiles the said address (ADR) for the said external memory by entering into the w least significant output locations the w least significant locations in the output of the said second counter, and, in the remaining output locations, shifts by the said w locations the outputs of the said adder-subtractor and the said second word in the said pair, the most significant output locations in excess of maximum addressable capacity being lost.

7. The processing unit defined in claim 6 wherein the said address unit (ADR) provides for cyclically addressing one or more of the said tables by storing, in a first register of the said third internal memory (MEMOF), the address of the first word (TOP) in the block being read, and, in a second register of the said third internal memory, the address of the first word (FREE) in a block available for writing, and by incrementing via the said incrementer (INC2) the content of the said registers subsequent to respectively reading or writing a block in the said table: a single word in the said block being addressed by incrementing the said second up counter (DISPA), and a single table being addressed via the content of a corresponding word pair in the said second internal memory (MEMIN).

8. The processing unit defined in claim 4, wherein said register block (MREG) in the said connection circuit (IOREG) also comprises a first circuit for checking the logic level of an overflow bit and the two most significant bits in one of the said selectable registers; the said first check circuit, when enabled by the said sequencing unit, generating a first alarm signal (ACT44) if the said overflow bit is active, or a second alarm signal (ACT34) if the said two most significant bits are active and the said overflow bit inactive; in that the said unit (ADR) for addressing the said external data memory also comprises a circuit for comparing the content of two internal registers in the said third internal memory (MEMOF), wich circuit, when activated by the said sequencing unit (SEQ) during cyclic addressing, emits a third alarm signal (WORK44) in the event of register content matching, the said internal registers containing the respective addresses of the first word (TOP) for reading and the first free word (FREE) in the cyclically addressed table; and in that the said unit (ADR) also comprises a second check circuit (CWORD34) which, when activated by the said sequencing unit (SEQ) upon the said adder-subtractor (SOMSOT) subtrating the said addresses of the said first word (TOP) for reading and the said first free word (FREE), checks that the two most significant bits in the result of the said subtraction are both zero, in which case it emits a forth alarm signal (WORK34); the said first, second, third and fourth alarm signals consisting of bit pairs in 1out-of-2 code.

9. The processing unit defined in claim 8 wherein also comprises a circuit for checking the results of the said test microprogram (DIAG) and substantially comprising:
 a first circuit (CRC) for calculating a cyclic redundancy code of the data on the said first internal bus (BUSIN) during internal testing and which, on receiving a comparison command (TST) from the said sequencing unit (SEQ), compares the said code with a further bit configuration on the said first internal bus, and emits, in the event of a negative result, a fifth alarm signal (ECRC) in 1-out-of-2 code;
 a second circuit (ENC1) for coding the said first, second, third, fourth and fifth alarm signals in a state word (SW) which it sends on to the said second internal bus (BUSOUT), and which produces, in the event of an alarm, an interrupt signal (FINT) which is supplied to the upper hierarchical level.

* * * * *

UNITED STATES PATENT AND TRADEMARK OFFICE
CERTIFICATE OF CORRECTION

PATENT NO. : 4,907,278
DATED : March 6, 1990
INVENTOR(S) : Riccardo Cecinati, et al.

It is certified that error appears in the above-identified patent and that said Letters Patent is hereby corrected as shown below:

Title Page - Assignee's name should read:

--(73) Assignee :

--Presidenza Dei Consiglio Dei Ministri Ufficio Del Ministro Per Il Coordinamento Delle Iniziative Per La Ricerca Scientifica E Tecnologica, Dello Stato Italiano, Rome Italy --.

Signed and Sealed this

Thirty-first Day of March, 1992

Attest:

HARRY F. MANBECK, JR.

Attesting Officer

Commissioner of Patents and Trademarks